(12) United States Patent
Lachenbruch

(10) Patent No.: US 7,273,490 B2
(45) Date of Patent: Sep. 25, 2007

(54) HEAT WICK FOR SKIN COOLING

(76) Inventor: Charles Arthur Lachenbruch, 126 Linwood La., Summerville, SC (US) 29483

( * ) Notice: Subject to any disclaimer, the term of this patent is extended or adjusted under 35 U.S.C. 154(b) by 0 days.

(21) Appl. No.: 11/147,707

(22) Filed: Jun. 8, 2005

(65) Prior Publication Data

US 2005/0288749 A1 Dec. 29, 2005

Related U.S. Application Data

(60) Provisional application No. 60/577,765, filed on Jun. 8, 2004.

(51) Int. Cl.
*A61F 7/00* (2006.01)

(52) U.S. Cl. .................................. 607/104; 607/108
(58) Field of Classification Search .............. 607/104, 607/108–112, 114
See application file for complete search history.

(56) References Cited

U.S. PATENT DOCUMENTS

| 5,691,040 A | * | 11/1997 | Barbeau et al. | ............. 428/198 |
| 6,145,143 A | | 11/2000 | Hicks et al. | |
| 6,763,671 B1 | * | 7/2004 | Klett et al. | ................ 62/259.3 |
| 2003/0046762 A1 | | 3/2003 | Stolpmann | |

FOREIGN PATENT DOCUMENTS

| DE | 195 14 295 A1 | 10/1996 |
| EP | 0 621 026 A | 10/1994 |

* cited by examiner

*Primary Examiner*—Roy D. Gibson
*Assistant Examiner*—Aaron Roane
(74) *Attorney, Agent, or Firm*—B. C. Killough

(57) ABSTRACT

Steady-state cooling of the skin is achieved by a support surface without requiring external power or circulation of air. Heat is transferred from via a thermally conductive layer or layers of material(s) that are soft, pliable, and comfortable to sit or lie on. The layer is connected to conductive materials that transport heat and diffuse the heat to a cooler environment.

17 Claims, 24 Drawing Sheets

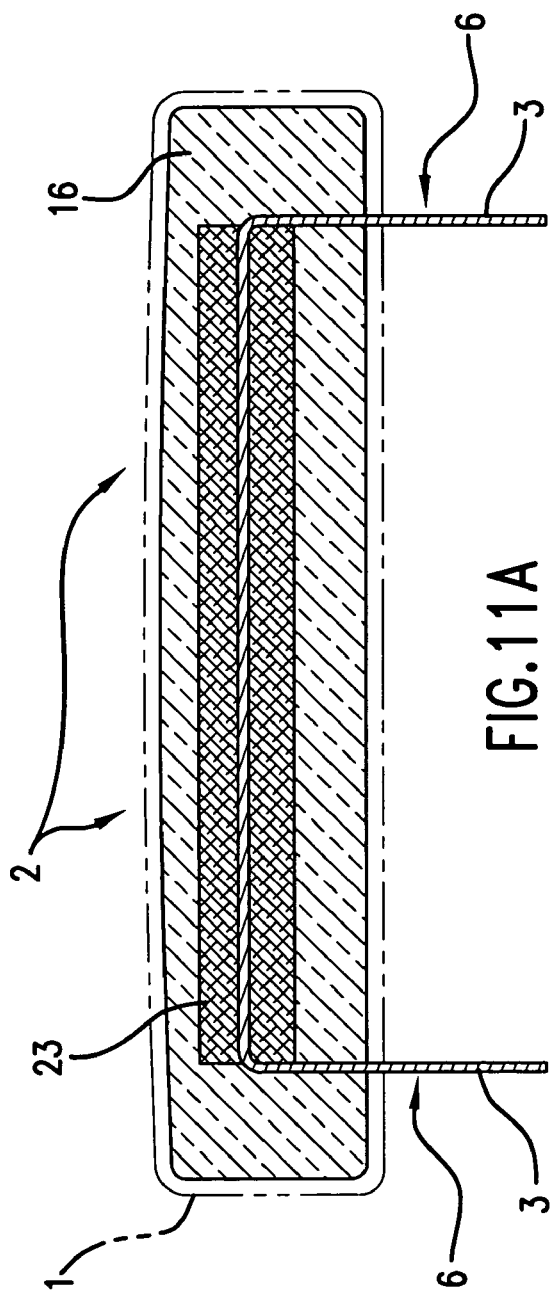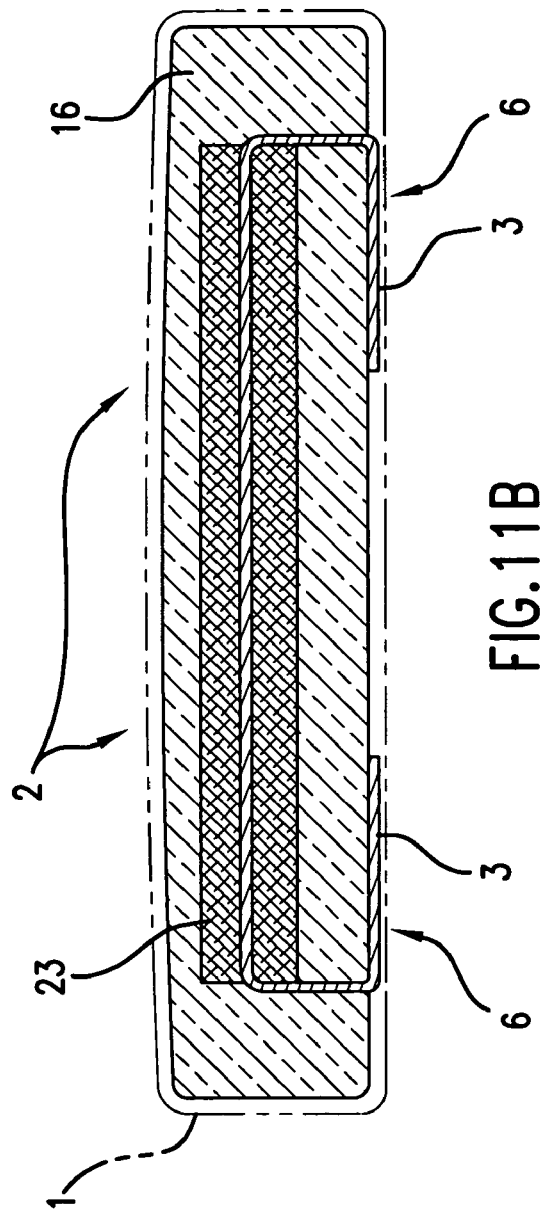

HEAT WICK FOR SKIN COOLING

Applicant claims the benefit of U.S. Provisional Application Ser. No. 60/577,765 filed Jun. 8, 2004.

Applicant claims the benefit of Serial Number PCT/US2004/003628 filed Feb. 10, 2004

Applicant claims the benefit of a Serial Number PCT/US2005/19413 filed Jun. 2, 2005.

FIELD OF THE INVENTION

The present invention relates to support surfaces that remove heat from human or other mammalians.

BACKGROUND OF THE INVENTION

Bedsores, or decubitus ulcers, can be a serious problem in bedridden or wheelchair-bound patients, particularly for people who are paralyzed, emaciated, post-surgical, elderly, or diabetic. The ulcers frequently penetrate through not only the skin, but the underlying muscle and bone as well. With the serious infections that often ensue, pressure ulcers can become life-threatening.

As the elderly population increases with demographic trends, the incidence is likely to increase. The results of National Pressure Ulcer Surveys in the United States from 1989 to 1997 indicate that despite the growth in the wound care and therapeutic surface industries, the incidence of pressure ulcers appears to have increased over this period. It is clear that while new treatment solutions may be relatively effective, their cost precludes their use by the vast majority of caregivers in the settings in which pressure ulcers and other chronic wounds must be managed. Disproportionately, this includes the nursing home, home care, and of course, the overseas markets where resources are limited. The consensus among thought leaders in the international medical community supports the contention that less expensive medical solutions are required generally and urgently. The invention to be described here is intended to fulfill this societal need.

Bedsores, or pressure ulcers, were named because they most commonly develop where tissue pressures are greatest—over the bony prominences, such as the heels, sacrum (tailbone), ischia, greater trochanters, and ankles (external malleoli). At these sites where the pressure on the skin is concentrated, blood flow can be restricted. If nutrient deficit exceeds tissue demand over a given interval, the tissue will start to die locally, resulting in an ulcer.

It is generally recognized that it is important to limit both skin warming and moisture accumulation to effectively combat skin breakdown. This has been embraced by professional bodies and recognized thought-leaders in the wound care medical community.

The normal core temperature of the human body is between 36° and 38° C. Skin temperature typically ranges between about 30° C. and about 34° C., depending on ambient temperature, the amount and type of clothing being worn, the core temperature, and where the skin is located on the body. However, on a typical mattress, seat cushion, seat back, etc., heat is trapped between the body and the covered skin surface and the skin temperature rises rapidly and may reach 35 to 37 degrees C. This small temperature elevation that occurs with the skin in contact with the mattress, seat cushion, etc., has important physiologic effects.

When a patch of skin is warmed beyond a specific level referred to as the "perspiration threshold" of approximately 32 to 34° C., local perspiration in the region increases markedly. The accompanying moisture softens the skin (maceration), which makes it more susceptible to breakdown. The build-up of moisture increases the friction between the skin and the surface materials resulting in increased shear stresses in the tissue. It has also been shown that elevated skin temperature is associated with increased metabolic demand, therefore, researchers have speculated, increasing the susceptibility of the tissue to ischemic injury, particularly when both nutrient supply and metabolite removal are reduced by loading. Generally, tissue metabolic rates increase by approximately 10% for each one degree Celsius increase in temperature. Warmed tissue generates an increased demand for blood supply that can be met when the skin is not under significant load. At interface pressures of 20 or more mm Hg, as occur under the bony prominences on a mattress or seat, blood flow can not be increased to meet this demand and the tissue becomes ischemic. A study demonstrated that skin tissue with reduced blood supply has been shown to be less susceptible to injury when tissue temperatures were slightly reduced. In a second study, identical pressures were applied to the skin tissue of research animals at nearly 300 sites. The skin temperatures at the interface varied between 28 and 36 degrees C. The results showed a very strong positive correlation—nearly perfect, in fact—between skin temperature and degree of skin breakdown.

When skin temperatures are maintained within certain limits, the person or animal is more comfortable. For humans, comfort is optimal when the skin temperature is maintained close to its natural (non or lightly insulated) temperature of 30 to 34 degrees C., even when insulated support conditions are employed. The devices described herein have important medical and non-medical applications. The non-medical applications include most seating and bedding applications, such as mattresses for the home, mattress overlays, tickings, pillowcases or pillows, or seating or seat backs for the office, home, and vehicle markets.

Temporary skin cooling can be accomplished by increasing the heat input required to increase the temperature of the surface. The quantity of heat required to increase the temperature of a given quantity of material by a specific temperature is called the specific heat. The specific heat can be expressed in Joules/kg-degree K. The quantity of heat required to raise the temperature of a given body is referred to as the heat capacity of the body. If a large sample and a small sample are both made of the same material, for example, the larger sample will have a greater heat capacity although both will have the same specific heat. A surface composed of high specific heat material such as silicone gel or fluid, or even a waterbed, will provide temporary cooling because a great deal of the body's heat will flow from the skin, initially at approximately 30 to 34° C. to the surface, initially at 23° C. room temperature. The skin will continue to be cooled as long as the surface remains cooler than the skin. Materials with low specific heat, such as a urethane foam, warm rapidly toward body temperature and therefore cool the skin only very briefly.

In order to provide continuous, steady-state cooling, heat is removed and transferred to the environment or to another system that is external to the surface to be cooled. A need exists for non-powered, or, stated otherwise, self-powered, relatively inexpensive devices to provide steady state cooling at the level of the expensive, externally powered LAL surfaces currently in use. It is valuable to develop such a device, whether powered or not, that provides cooling without spreading airborne pathogens from the occupants' skin surface into the common environment, as appears to be the case with low air-loss surfaces due to their reliance on high volume blowers or air-pumps. Adding a small powered thermoelectric module to enhance heat withdrawal by the invention improves performance in all environments with greatly reduced overall air-flow, and hence, reduced risk of spreading air-borne infection The likelihood of bedsore formation is reduced by lowering tissue metabolic rate (and therefore reducing the nutrient-deficit in tissue that is pressure-loaded and subject to reduced blood flow) and by limiting local perspiration, which weakens the outer skin layer (the stratum corneum) over time. These inventions may be used as an aid in the prevention of bedsores or other skin ulcers.

Moderate cooling of the skin during support (from 35° C. to 37° C. down to the 30° C. to 34° C. range) also makes the user more comfortable. This would be true in both bedding and seating applications, in medical and consumer environments. When used over broader areas of the skin, the cooling devices, whether over the skin (blanket or duvet-insert) or under the skin (mattress or seating overlays) may be useful as an aid in combating fever in both home and medical environments. The proposed inventions therefore have not only medical applications, but applications in a multitude of general consumer niches as well.

SUMMARY OF THE INVENTION

The "heat wick" of the present invention provides steady-state cooling of the skin generally without requiring external power or circulation of air. In a non-powered surface according to the invention, the skin is cooled passively by conduction (not convection) without external power. Heat may be withdrawn from the device using a thermo-electric module or other compact chilling device. Heat is transferred from the body via a highly thermally conductive layer or layers of material(s) (referred to in this specification as the Conducting Component) that are soft, pliable, and comfortable to sit or lie on. The layer is connected with conductive materials that are configured to transport heat and diffuse the heat to a cooler environment.

The heat wick may be positioned within a powered surface to enhance cooling. The device may be embedded in, on placed upon, a surface in which the power drives a stream of air that convectively cools the region adjacent to the patient and the patient. The heat wick may be configured to efficiently draw heat from region adjacent to the patient into the stream of moving air. The air-stream enhances heat withdrawal from the diffuser region.

DESCRIPTION OF THE DRAWINGS

FIG. 2A is a sectioned view of a mattress according to another embodiment of the invention.

FIGS. 4 and 5 are sectioned views of mattresses according to additional embodiments of the invention.

FIG. 11A is a sectioned view of a mattress according to an embodiment of the invention shown in FIG. 11.

FIG. 11B is a sectioned view of a mattress according to another embodiment of the invention shown in FIG. 11.

DESCRIPTION OF THE PREFERRED EMBODIMENTS

Figure 1:
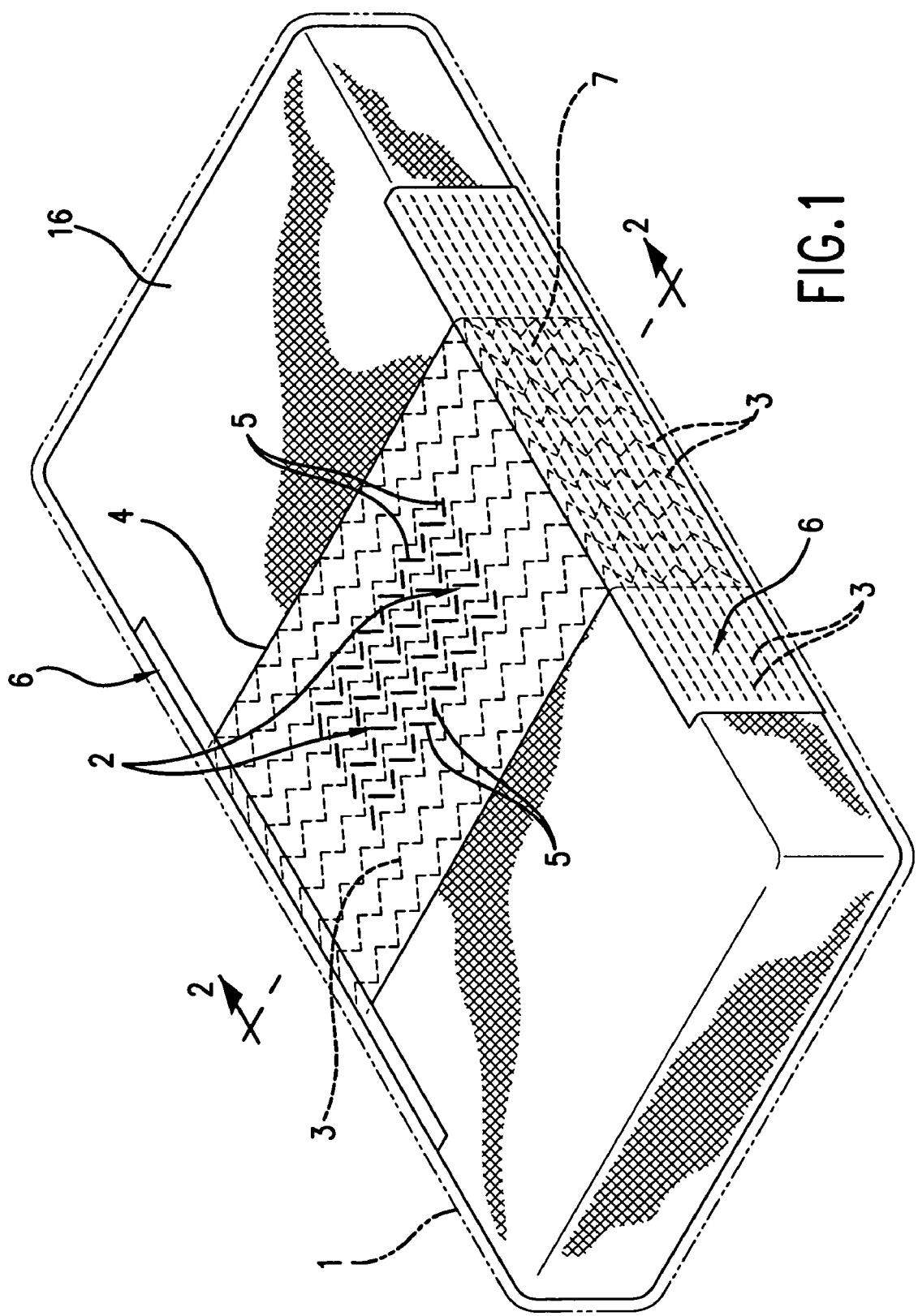
FIG. 1 is a perspective view of a mattress with one embodiment of the cooling surface shown in the central position of the mattress 16.

FIG. 1 is a perspective view of a mattress with one embodiment of the cooling surface shown in the central position of the mattress 16. The cooling portion may be at any position on the mattress, depending on the portion of the anatomy to be cooled. In the central position shown, the device is positioned to cool the sacral and low back region of the body.

In this embodiment, the device is positioned beneath the ticking 1. In other embodiments, the device is positioned as an overlay on top of the ticking or other surface.

Oriented across the mattress in the support region 2 are a series of highly thermally conductive materials 3. These conductive materials may be pitch-based carbon fibers or polymers with thermal conductivities in excess of 40 W/m-K. Although the predominant orientation is across the mattress (i.e., perpendicular to the long axis of the mattress), they have a zig-zag or somewhat sinusoidal or wavy configuration. This geometry allows the support region 2 to stretch in the predominant fiber direction (in this case, perpendicular to the long axis of the mattress) without imposing undue stress on the conductive materials (i.e., the fibers or polymers) themselves. This geometry provides structural support to the conductive materials that is not afforded when the fibers run strictly transverse to the mattress without zig-zag or wavy motions.

In the zig-zag configuration, the conductive fibers, polymers, or nanotubules may be chopped to the length of each zig-zag. At each corner the overlap between fiber bundles should be substantial (greater than or equal to 2 mm) to ensure continuity of the heat conduction path.

In this embodiment the conductive material is preferred to be encased in a thin envelope or attached to a layer 4 of protective sheeting (such as urethane) or fabric (such as Lycra). The envelope may be a closed or an open sheath, like a duvet cover that provides protection and can be laundered, allowing the conductive material to avoid the harsh cleaning process. A stretchy material is preferred because it provides additional protection to the conductive materials. For envelopes or protective sheets made of less compliant materials such as urethane, small slits 5 may be provided that allow for distension of the envelope or sheet when a load is placed upon it.

Figure 2:
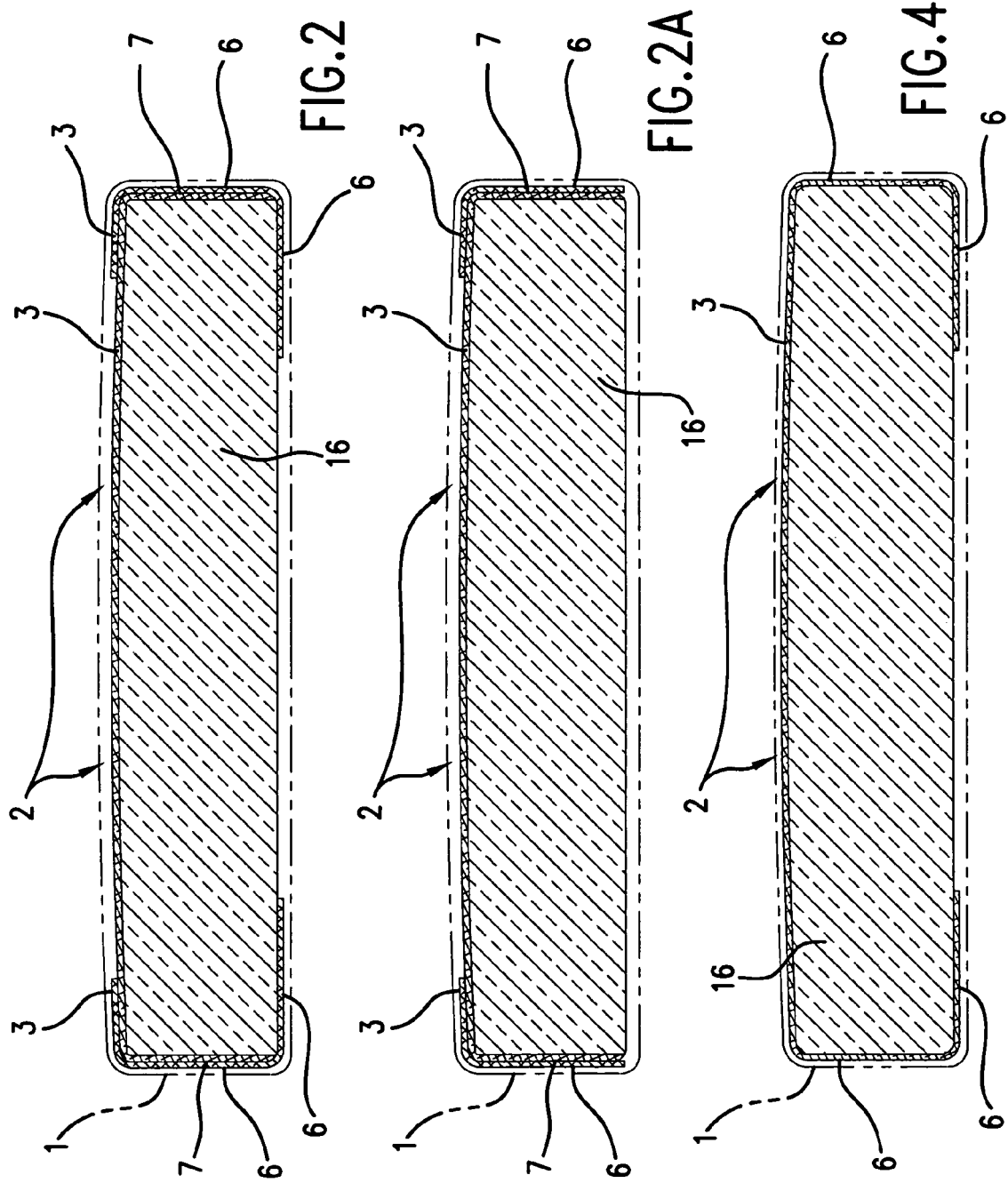
FIG. 2 is a sectioned view of a mattress according to one embodiment of the invention.

Near the edges of the surface, the conductive elements of the support region 2 overlap with those of the thermal diffuser region 6. This region receives heat that is transported conductively from the support region that is adjacent to the body. For ease of manufacturing, the same highly conductive material as the support region may be used so that heat is rapidly distributed over a relatively broad, but cooler, area and diffused into the still cooler environment. The diffuser region is peripheral to the support region and may present at the edges or sides of the seat or mattress, or underneath, or suspended slightly to the side of the surface. The region of overlapping conductive materials 7 is most visible in FIGS. 2 and 2A. In FIG. 2, the diffuser 6 extends around and underneath the mattress. In FIG. 2A, the diffuser does not extend underneath the mattress.

The component that absorbs and transports the heat, and then exhausts it to the environment, is called the Conductive Component. No separate reference number appears in the drawings for the Conductive Component, which is comprised of the support region and the diffuser region, both of which are identified in the drawing figures. The Conducting Component may be considered as a pipe or a conduit that functions to transport heat in specific applications. One end of the Conducting Component is the end of the "pipe" that into which the heat flows (i.e., the support region) and the other end is region from which heat is deposited. The Conducting Component is not a simple one-dimensional "pipe," and it may have complex geometries that enable it to perform its heat transfer function efficiently for a given application.

Figure 3:
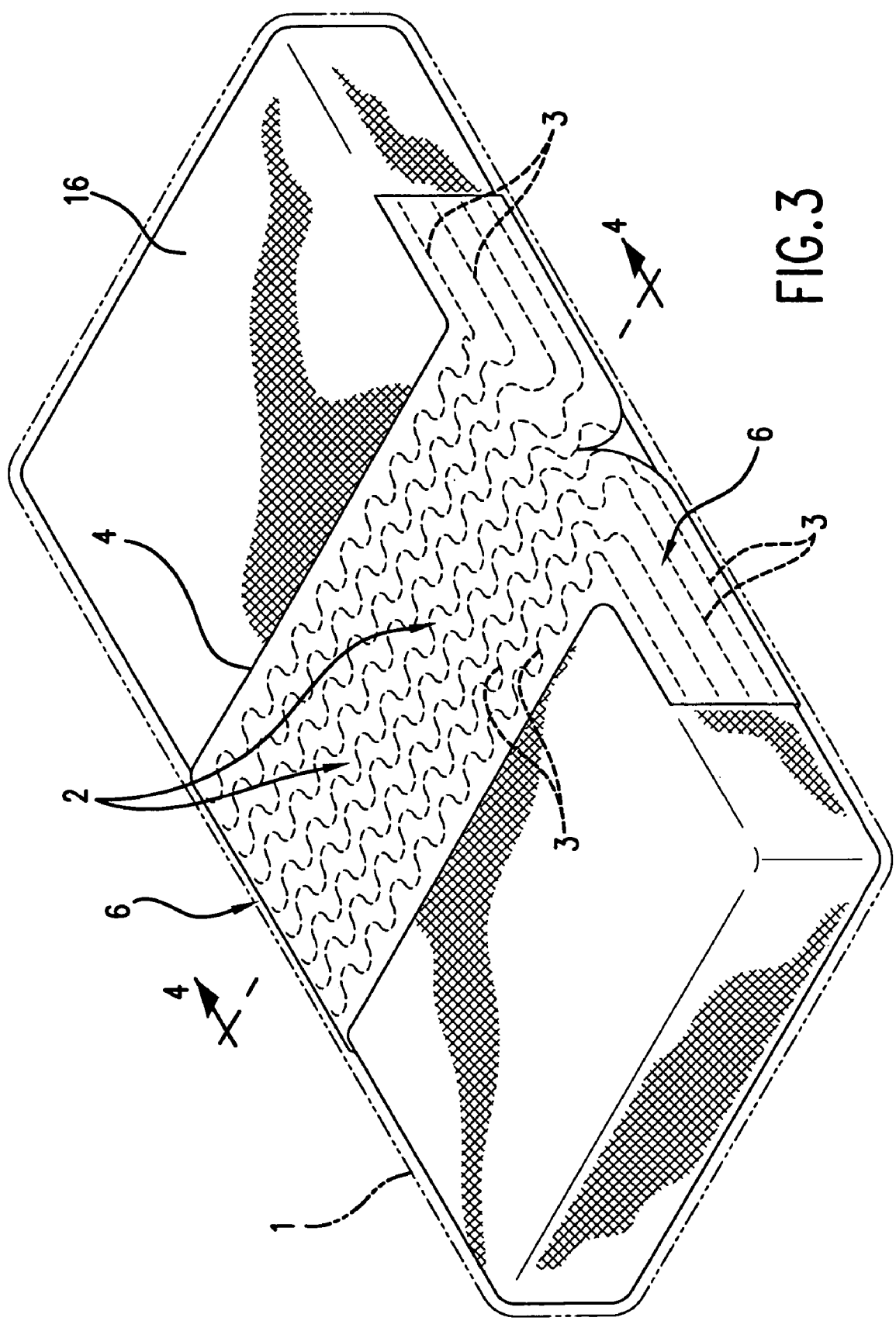
FIG. 3 is a perspective view of a mattress according to an additional embodiment of the invention.

Another embodiment is shown in FIG. 3. Conductive material 3 in the support region 2 is formed in a wavy configuration. The fibers are continuous with, but not overlapping, the fibers in the diffuser region 6. This continuity of fibers between support and diffuser regions is shown in FIG. 4. There is no distinct region of overlap 7. The fiber direction changes as the fibers reach the edge of the support region, and have a different orientation in the diffuser region. The continuity, or discontinuity, of fibers between these regions may be used with either the wavy or the zig-zag configurations. This configuration may not require that every single fiber is continuous across the surface. As in many yarn constructions, a number of shorter fibers may be bundled in tight proximity to span the required distance. However, it is preferred that there no distinct junction or junctions exist between fiber bundles in this embodiment.

Figure 5:
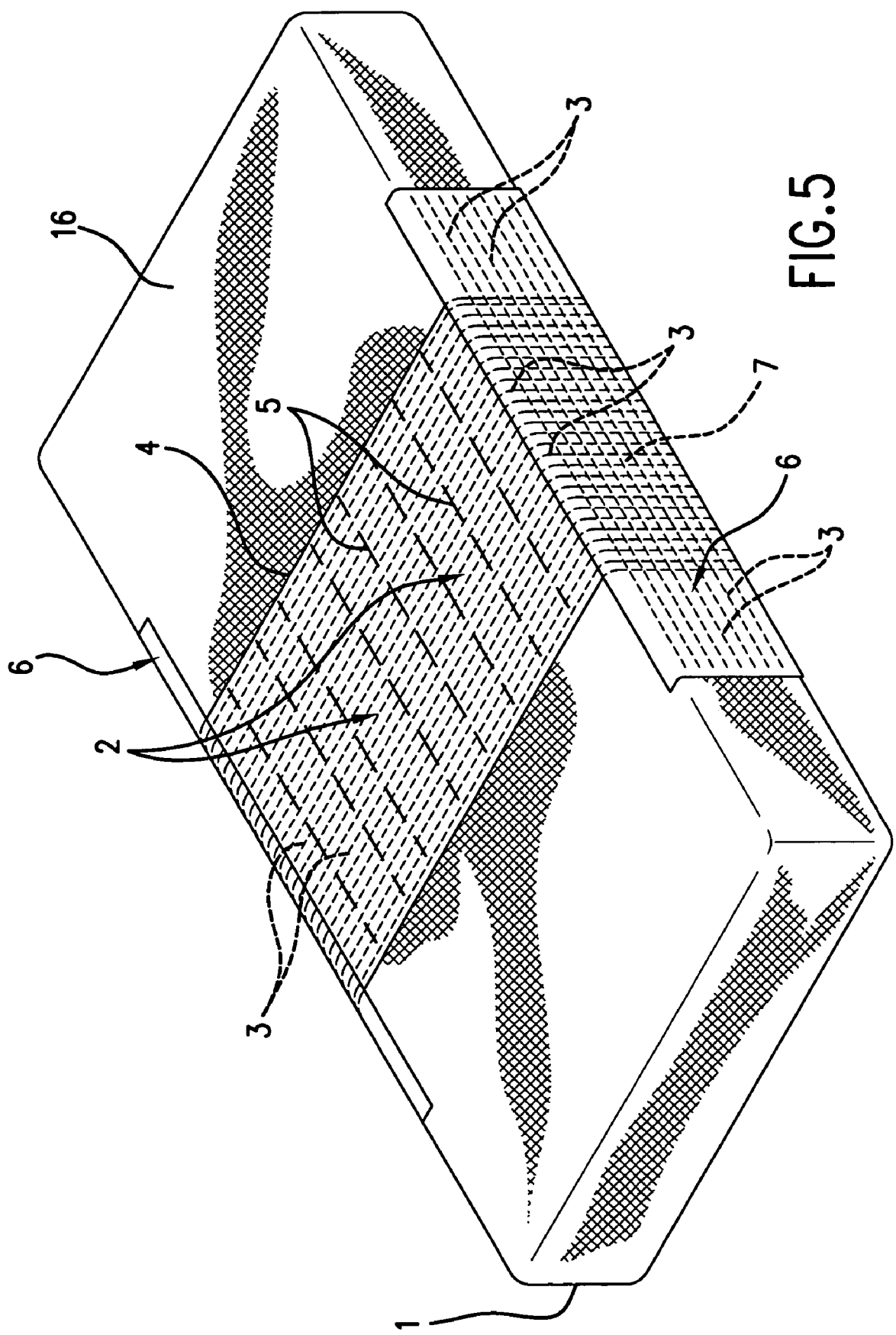

Another embodiment is shown in FIG. 5. The conductive materials 3 are generally arranged in a straight and parallel configuration and oriented across the support region 2. The support region shown is positioned on a mattress, but may be positioned a seat back or seat cushion or other similar support surface. The conductive materials may not be continuous, and may be overlapped sufficiently to allow for efficient heat transfer in the predominant direction of orientation. Small slits 5 may be present in the sheeting or fabric that carries the thermal material in the support region. Again, these slits relieve the mechanical stress that accompanies loading.

In this embodiment, the cooling surface is shown in use as a mattress overlay on top of the mattress ticking 1. It may be used beneath the ticking, as shown in FIGS. 1 and 2, and may be used either beneath, or on top of, a seat cushion or seat cover.

The diffuser region 6 may be at the edge or sides of the bed, and may extend underneath the mattress or seat cushion. For a seat back embodiment, the diffuser region extends to the reverse side of the seat back. The support and diffuser regions overlap with one another 7 and are oriented so that they most efficiently direct heat from warmer regions to cooler regions. A right angle intersection may allow for conduction of heat from the body outwardly, and then to direct the heat along the edges of the bed or other support.

Figure 5A:
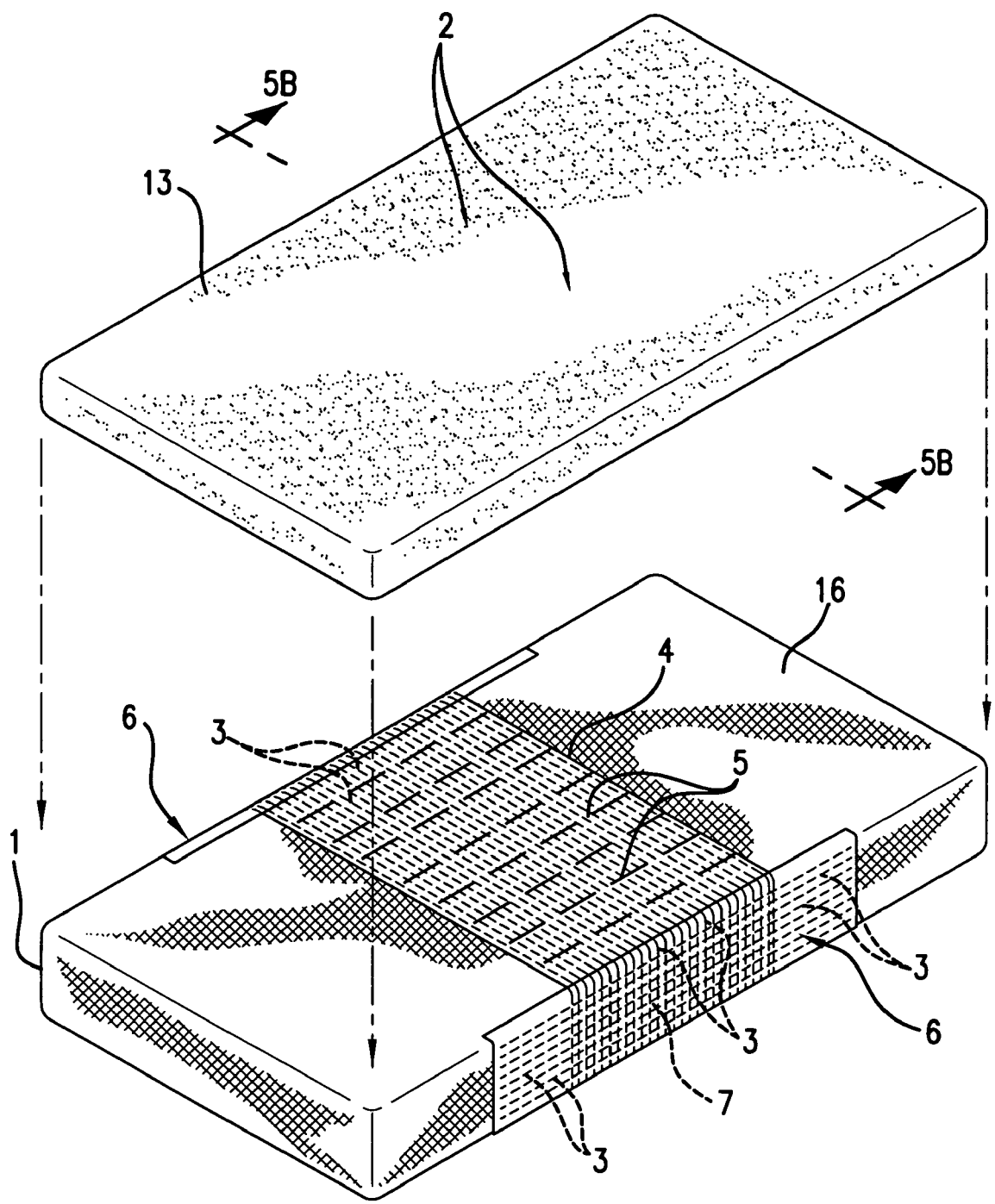
FIG. 5A is an exploded view of a mattress according to an additional embodiment of the invention.

FIG. 5A shows the embodiment of FIG. 5 in use on a standard mattress 16 and underneath a mattress overlay 13. A user may take advantage of both the cushioning properties of a preferred mattress overlay and the cooling characteristics of the conduction surface. When a body is positioned on an air or foam overlay, the overlay compresses to the greatest extent in the regions of greatest pressure. These are the warmer central regions of the body such as the sacrum that are in need of the greatest cooling. The compressed regions receive the greatest cooling because the insulation between the skin and the conductive material (i.e., the thickness of the compressed overlay) is thinnest in this region. Conversely, areas in need of less cooling such as the edges of the body and the forearms are insulated from the Conducting Element to a greater extent because air from the central region of the overlay is squeezed to the periphery. Because these less critical areas are insulated to a greater extent than the critical central regions, the cooling power is focused in the regions of high pressure and reduced overlay thickness. This effect, of course, may be augmented by intentionally designing pads or overlays to put on top of the conductive material in the support region, focusing the cooling effect on specific regions.

Figure 5B:
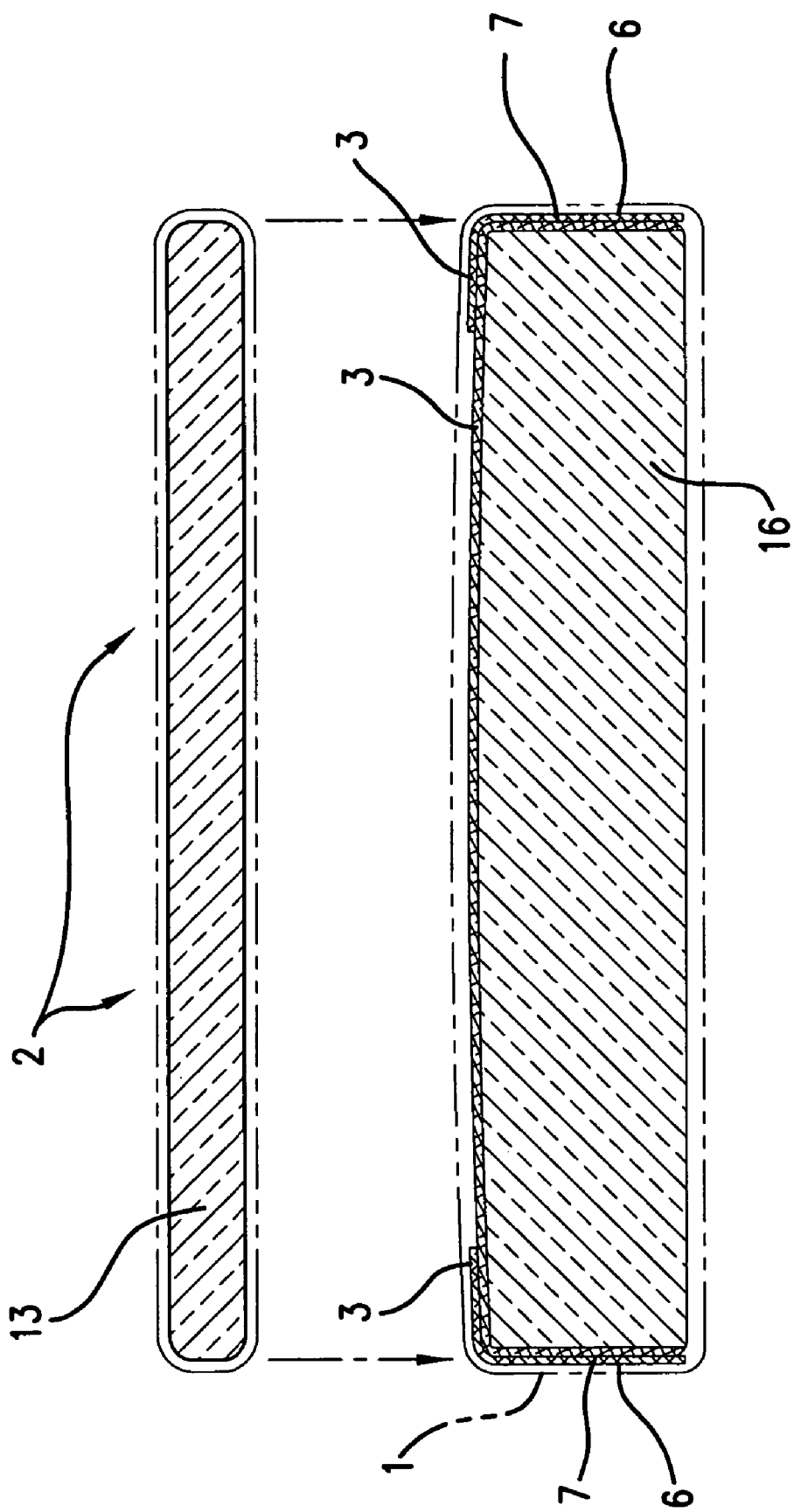
FIG. 5B is a sectioned view of the mattress as shown in FIG. 5A.

FIG. 5B is an end-view of the conduction device in use with a mattress and a mattress overlay.

Figure 6:
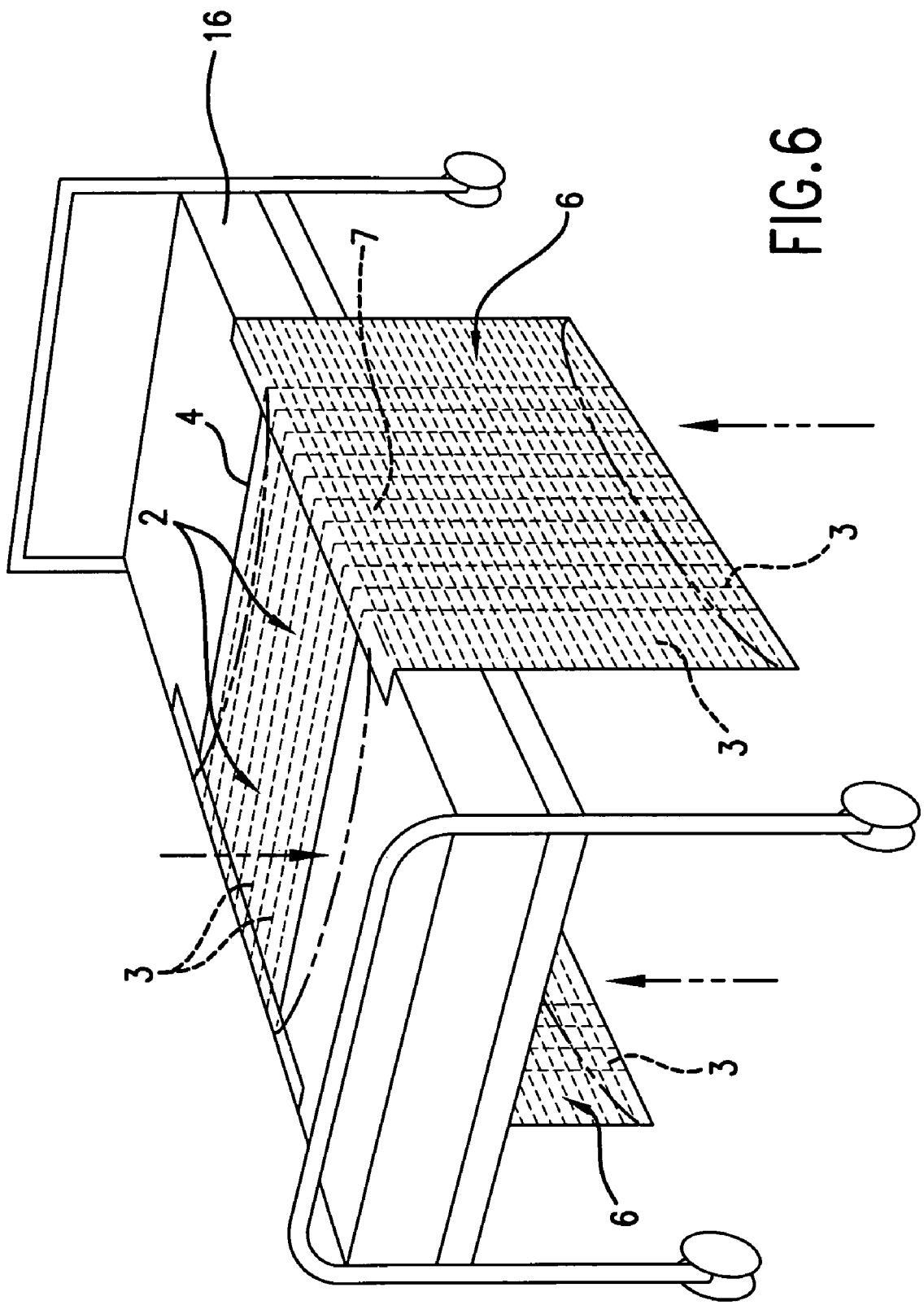
FIG. 6 is a perspective view of a bed comprising an embodiment of the invention.

In the embodiment of FIG. 6, the diffusers hang vertically from the edge of the bed and are not under the mattress. In this embodiment, the device is on top of the ticking. Various embodiments may be positioned inside or outside the mattress with similar effectiveness. Because the diffuser positions are not clamped between the mattress and the bed frame, when the user puts his/her weight on the support region and compresses the center portion of the device, and the edge diffuser regions are free to draw inward to accommodate this compression. Because the stress on the loaded conductive fibers 3 is much less with the diffusers 6 untucked, the fibers may not be wavy or zig-zagged.

Figure 6A:
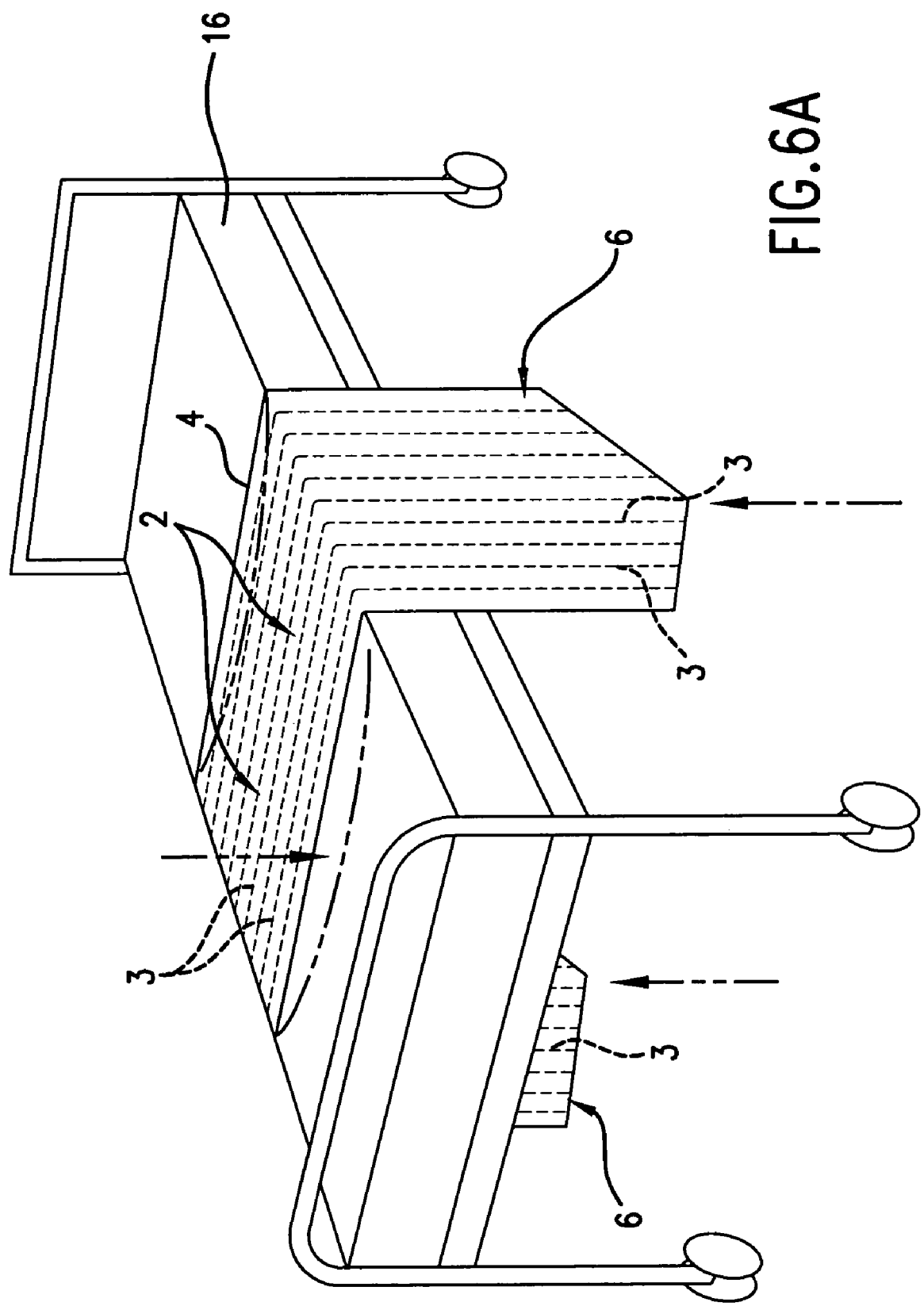
FIG. 6A is a perspective view of a bed comprising an embodiment of the invention.

FIG. 6A depicts another embodiment. Parallel fibers, or more generally, conductive materials 3, extend from the support region 2. The device is presented as a long rectangle, or double arrow-shape, if the diffuser is longer in the center.

This is compared with other embodiments where the device is an H shape, in which the cross segment of the H is the support region that runs across the bed, and the vertical segments of the H represent the diffuser regions. The two ends of the rectangle (or arrow) form the diffuser regions 6. They may be positioned underneath the mattress 16, or they may hang along the sides of the bed. In this configuration, the device is effectively a long "heat wick" made up of generally parallel conductive materials 3 that are shaped like a long scarf, and may be positioned at any point in the bed or seating surface to draw heat away from the selected anatomic site.

Note that all of the embodiments shown may be used underneath or over the ticking, and the diffusers may extend along the edge of the mattress, or they may be positioned under the mattress, or they may hang freely at the side of the bed, as shown in FIGS. 6 and 6A.

The diffuser region is preferred to be located at the periphery of the region to be cooled, and maintained at a distance from it. The diffuser region may be located on the vertical edges of the mattress or seat, and it may wrap to the underside of the mattress or seat, or around to the seat back for seat back cooling. There may be a portion of the diffuser at the edge of the mattress in the plane of the top surface (i.e., the horizontal plane) but these regions should be at the periphery of the mattress.

The support region 2 and the diffuser regions 6 are in thermal contact. They may be continuous, as shown in FIG. 3 in which the conductive material bundles simply change direction in the diffuser regions to aid in the distribution of heat over a broader area in these cool regions of the surface. Alternatively, they are continuous, but do not change direction, as in the long scarf-shaped heat wick configuration described above (FIG. 6A). Alternatively (FIGS. 5 and 6), the conductive material from the support region overlaps the conductive material in the diffuser region so that heat is transferred from support material to diffuser material across this overlap junction 7.

Figure 7:
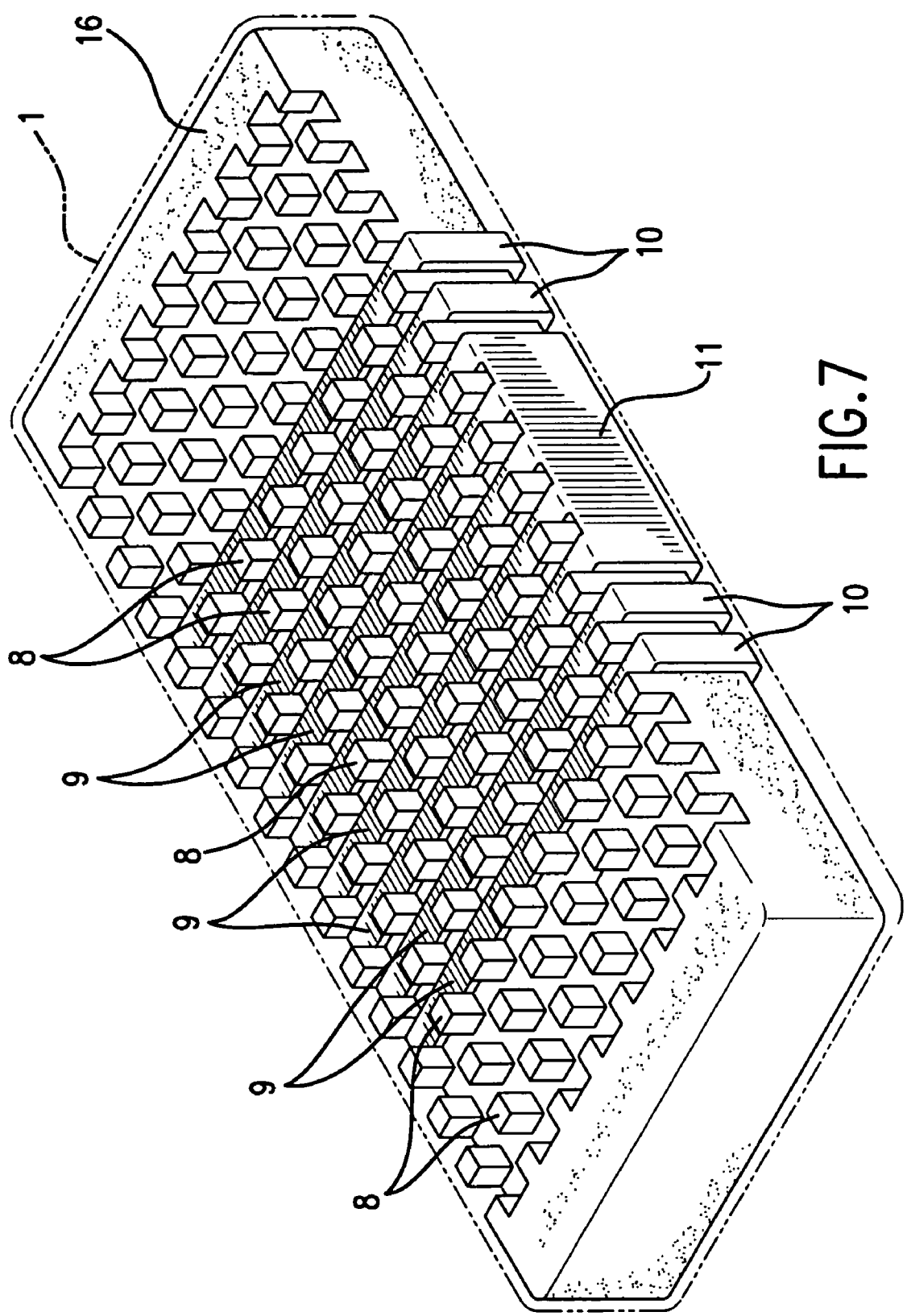
FIG. 7 is a perspective view of a multi-cellular mattress seat cushions, or seat backs.

The next series of embodiments (FIGS. 7, 8, and 9) depict embodiments that are appropriate for use with multi-cellular mattresses, seat cushions, or seat backs. A variety of quality support surfaces employ an array of relatively small air, foam, gel, or elastomer cells 8 that project toward the user and comfortably conform under weight loading. Because these surfaces sometimes overly warm the skin, a conductive cooling device may be integrated into the surface or used in conjunction with it. In FIG. 7, highly conductive strips 9 are positioned in the clefts between cells and are oriented to draw heat from the warm central support region 2 to the cooler periphery. The thermal diffuser region (10 and 11) may consist of the end portions of the conductive elements as they reach the peripheral regions 10, or underside of the bed. Alternatively, many of the individual strips may overlap a broader sheet of conductive material 11 intended to dissipate heat in the peripheral regions.

Figure 7A:
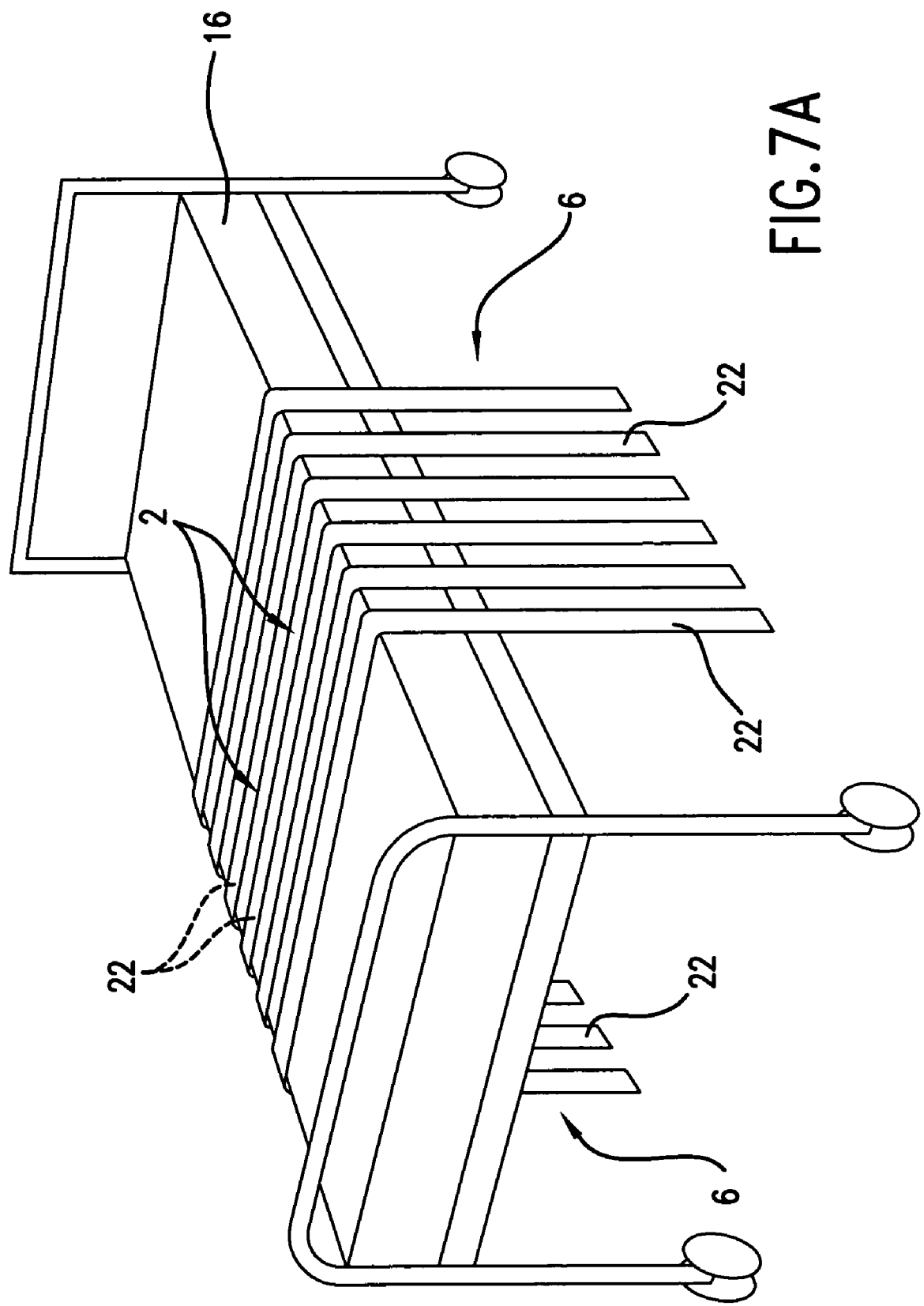
FIG. 7A is a perspective view of a bed comprising an embodiment of the invention.

In FIG. 7A, the multi-strip device is shown in use on top of a surface. In the depiction shown, the surface is a conventional mattress, but the multi-strip configuration may be used on top of a multi-cellular mattress, cushion, or overlay. The conductive strips 22 may or may not be covered for protection. Alternatively, the strips can be bound together loosely using a small amount of elastic thread from strip to strip.

Figure 8:
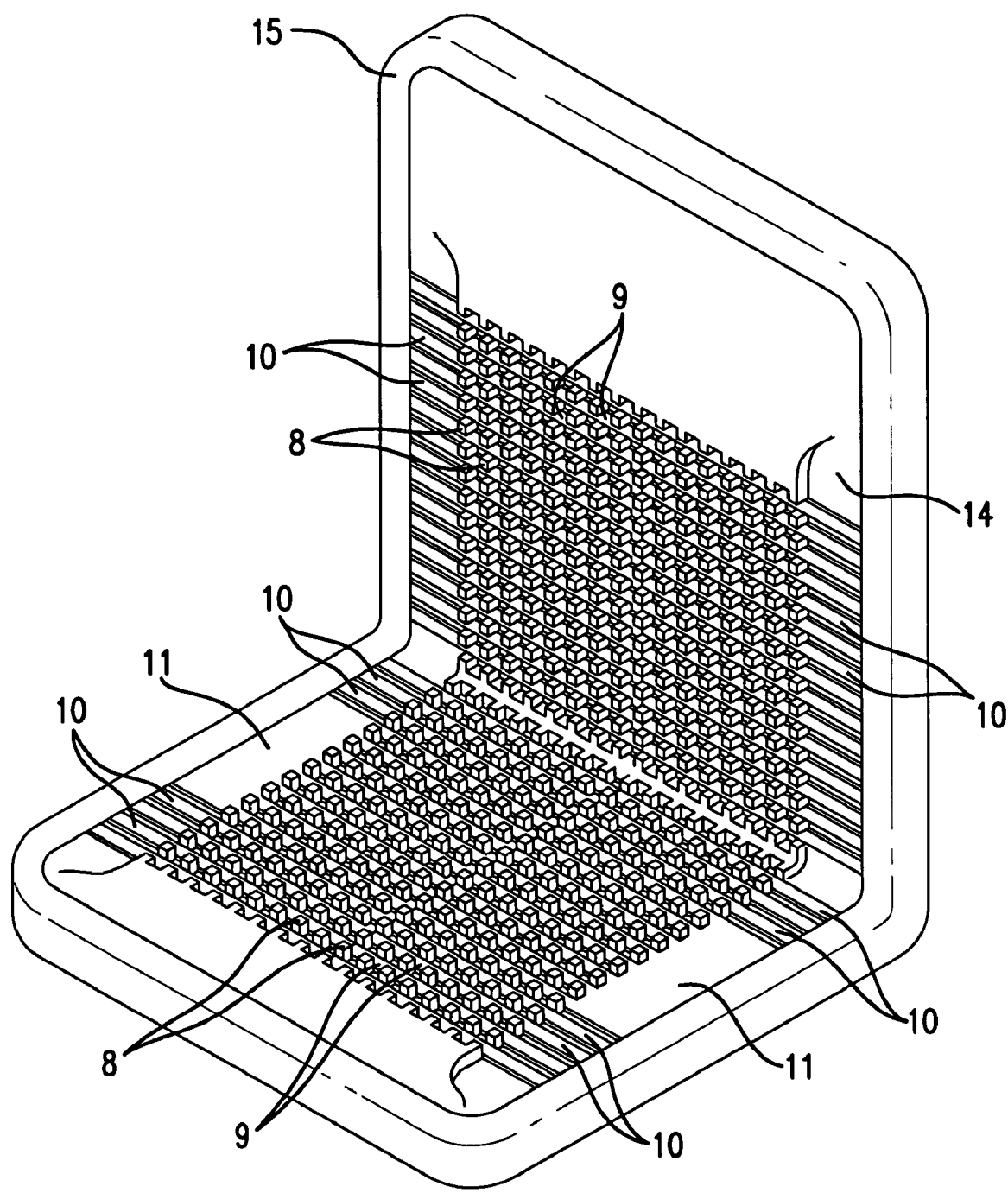
FIG. 8 is a perspective view of a multi-cellular seat cushions.

In FIG. 8, the device is incorporated into a cooling seat and seat back. Conductive strips 9 run between the cells 8 and draw heat to the cooler diffuser regions at the periphery 10 and 11. The conductive strips may be separated 10, or overlap a conductive sheet at the periphery, to enhance cooling area 11. The multi-strip configuration may be placed on top of the surface, or the strips may be embedded in the surface between the cells. Reference number 14 identifies the base cushion or base seat back which is present in the existing seat to prevent bottoming. Reference number 15 identifies the periphery of the seat, which may be constructed of a firmer foam or elastomer to add seating stability. The seating surface may comprise conductive material or be overlaid with conductive material 3 to aid in thermal diffusion to the environment.

Figure 9:
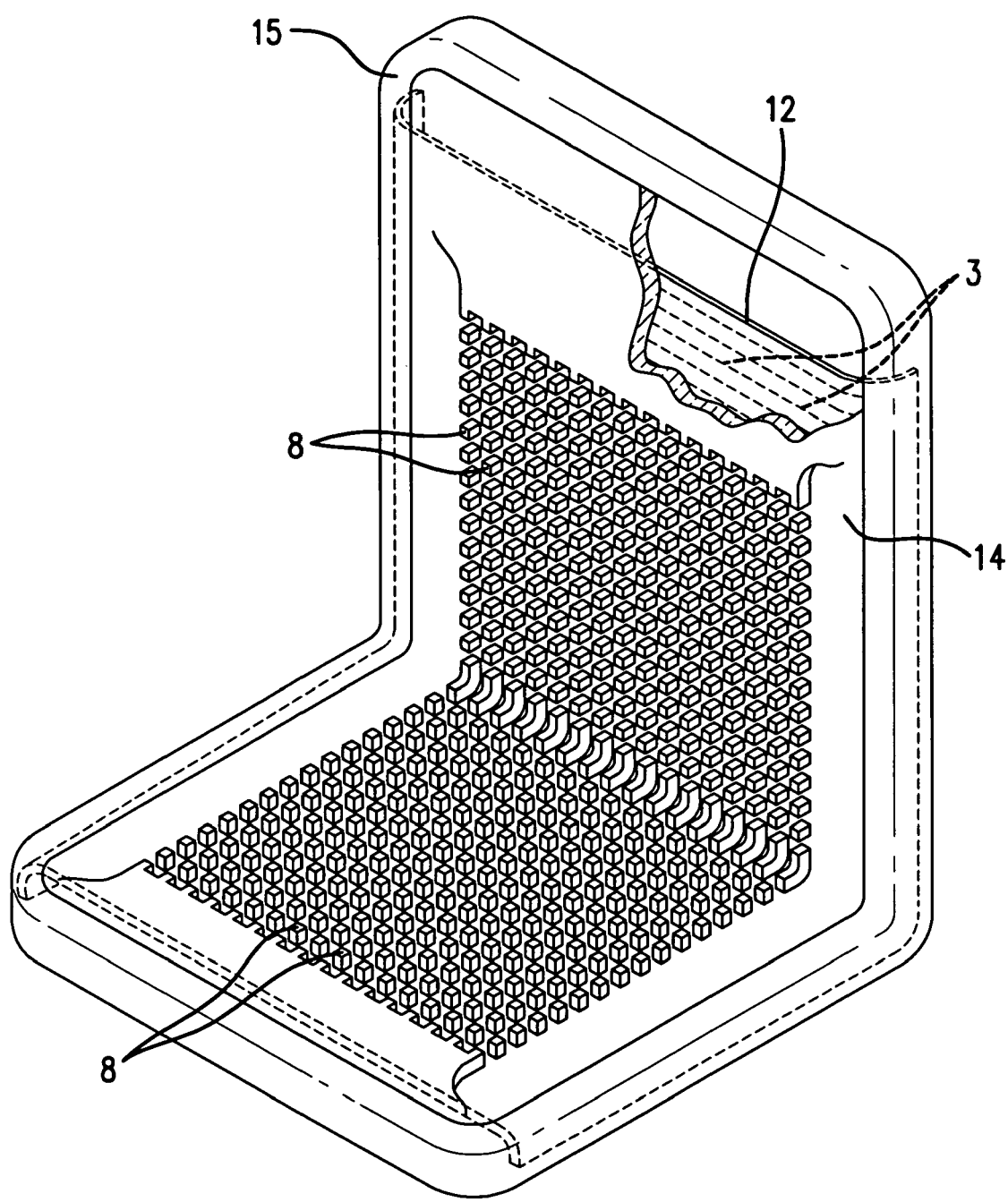
FIG. 9 is a perspective view of a multi-cellular seat backs.

In FIG. 9, the conductive material 9 is built into a base cushion 14 that runs beneath and between the cells 12. This base cushion may also form a rim at the periphery to add stability. The conductive elements 3 in the conductive layer 12 extend to the edge that surrounds the multi-cellular region and forms the diffuser region at the edge of the surface. The conductive layer may wrap into a lip at the outer edge of the seat cushion or to the rear of the seat back to increase the surface area exposed to ambient conditions for heat dumping to the environment.

Figure 10A:
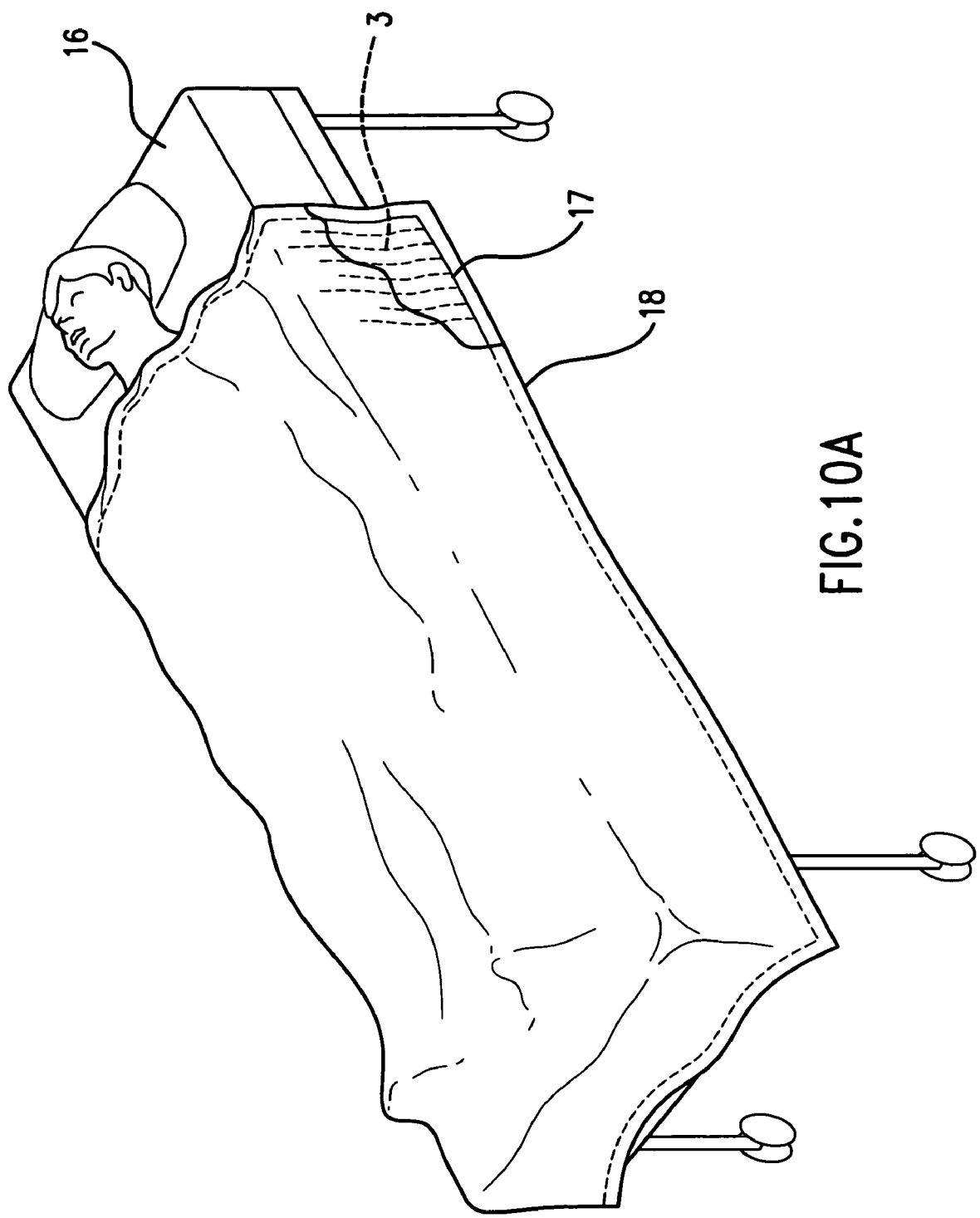
FIG. 10A is a perspective view of a duvet comprising an embodiment of the invention.
Figure 10B:
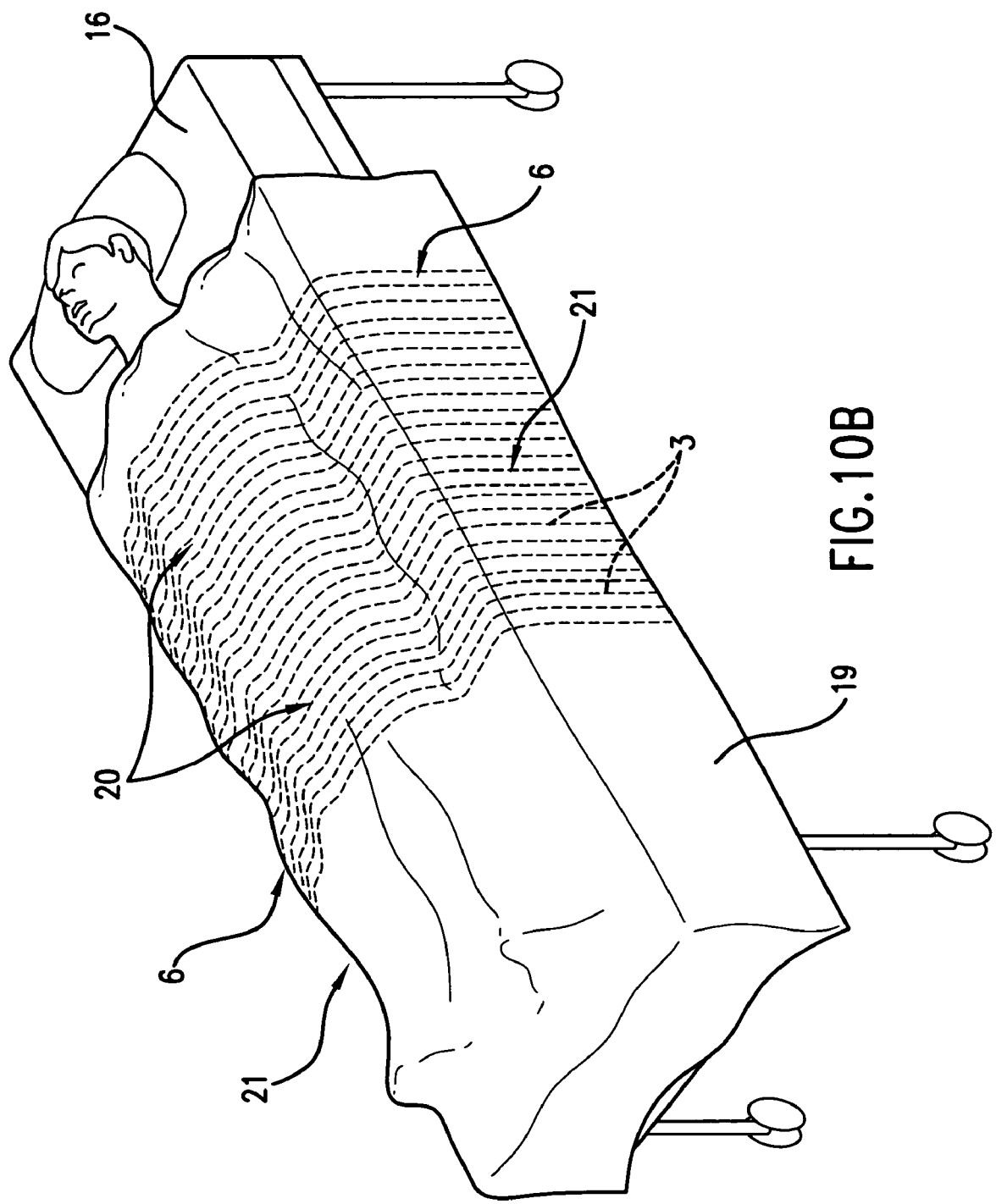
FIG. 10B is a perspective view of a bed cover comprising an embodiment of the invention.

The next series of figures demonstrate placement of the device over the user rather than underneath. The cooling blanket of FIG. 10A is shown as a duvet insert. The cooling insert 17 is inserted into a soft, launderable, and attractive duvet 18 (i.e., a blanket cover). Alternatively, the conductive materials 3 may be woven into a mat without cover (FIG. 10B) or attached to a sheet or blanket to provide structural support 19. In all configurations, the "support region" 20 of the cooling blanket is the region nearest the user and the diffuser region 21 is typically at the periphery to exhaust heat to the environment.

Figure 11:
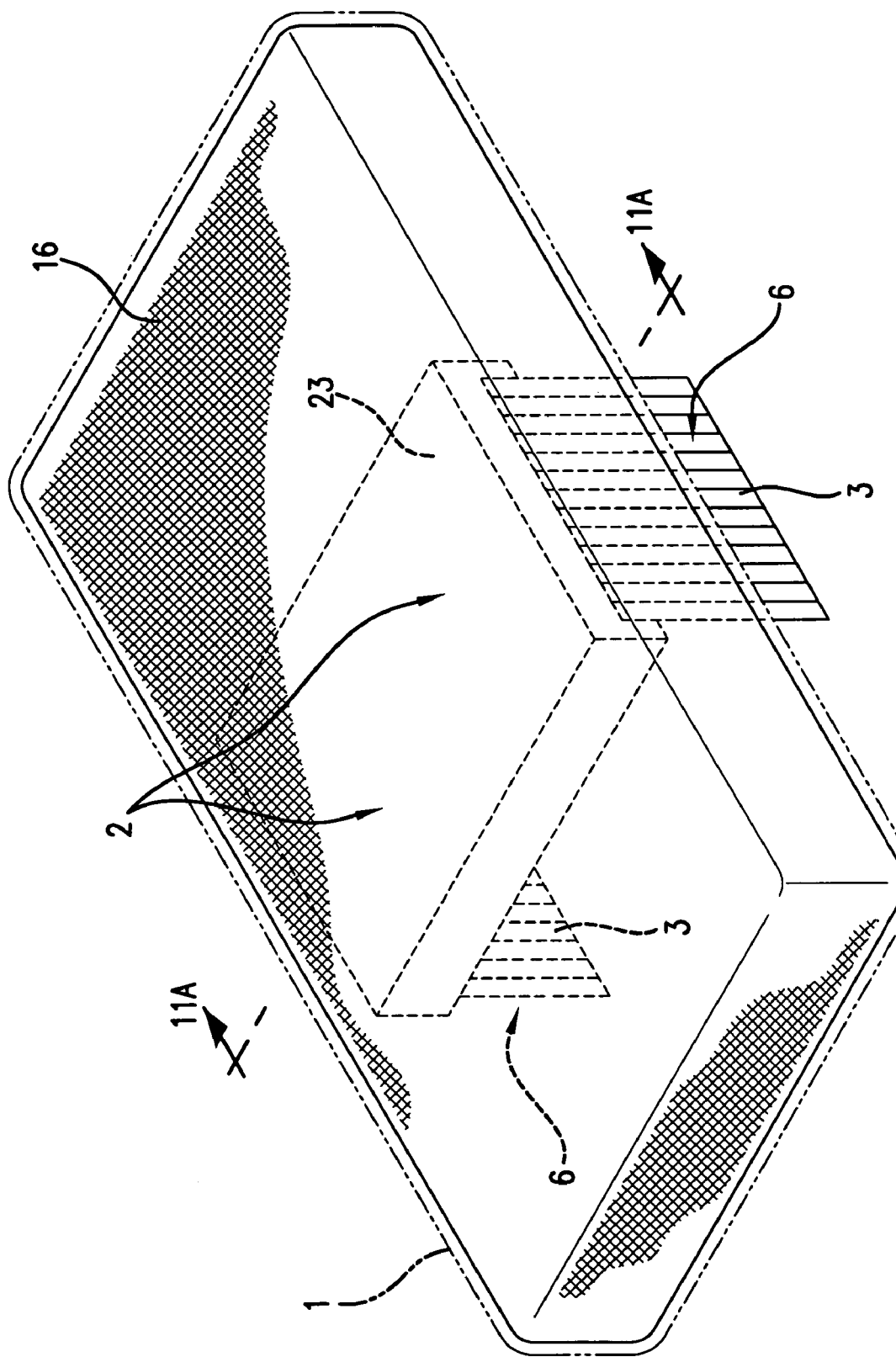
FIG. 11 is a perspective view of a mattress according to an additional embodiment of the invention.

FIG. 11 is a perspective view of another potential configuration of the cooling device. The device is embedded in a mattress 16. The diffuser regions 6 protrude directly through the mattress to the underside thereof. By protruding directly through the surface, the diffuser is located somewhat closer to the support region 2, which increases the thermal gradient and enhances cooling. It also lessens heat input to the heat wick from regions of the user's body, such as the elbows, that may need less cooling.

FIGS. 11A and 11B are cross-sectional views of two possible embodiment of the embedded device. In FIG. 11A, the diffuser regions 6 reach through the ticking and extend through the frame toward the floor. This is a particularly efficient configuration for cooling. In FIG. 11B, the diffusers wrap under the mattress and are inside the ticking.

Figure 12:
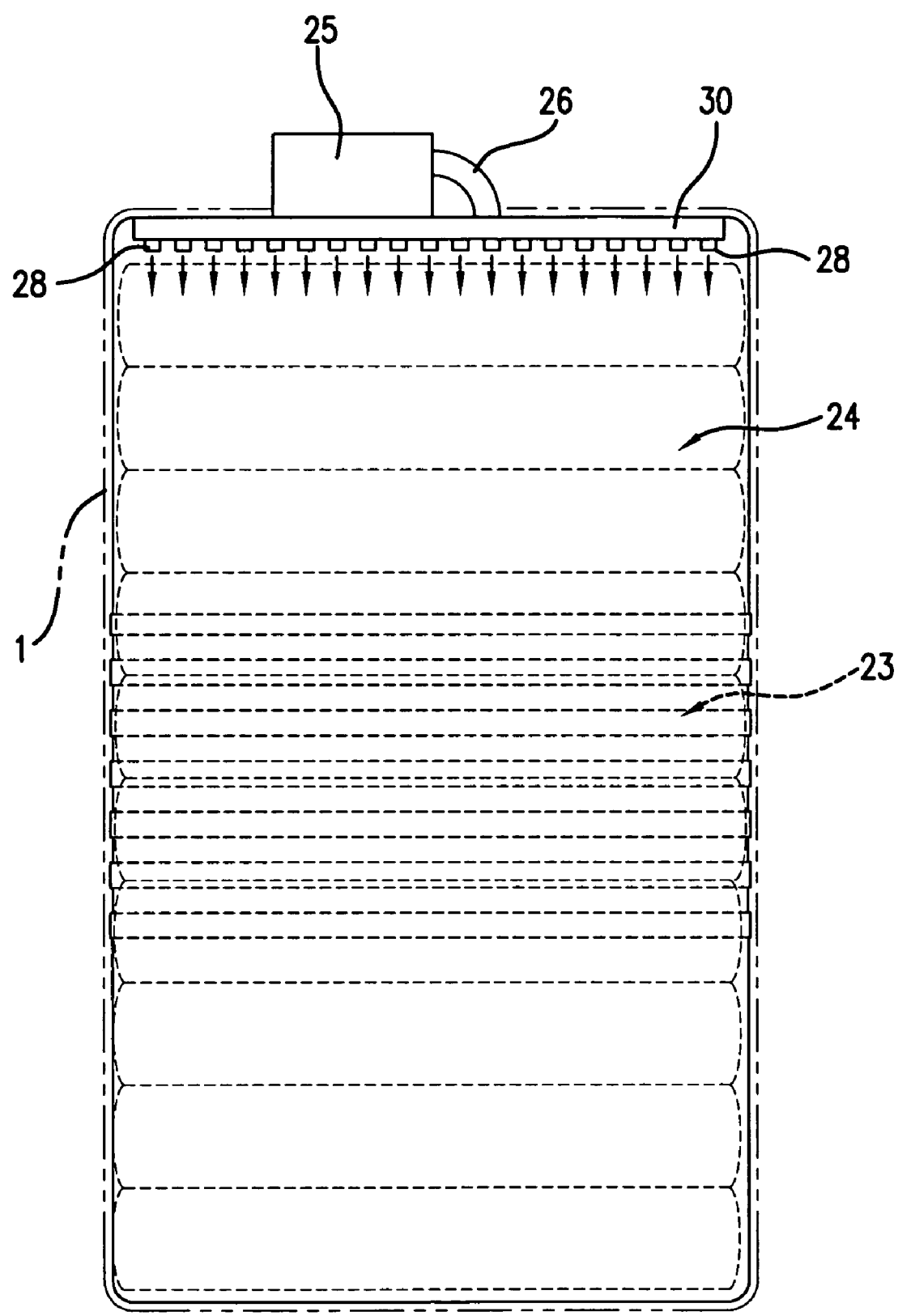
FIG. 12 is a plan view of a mattress according to one embodiment of the invention.
Figure 13:
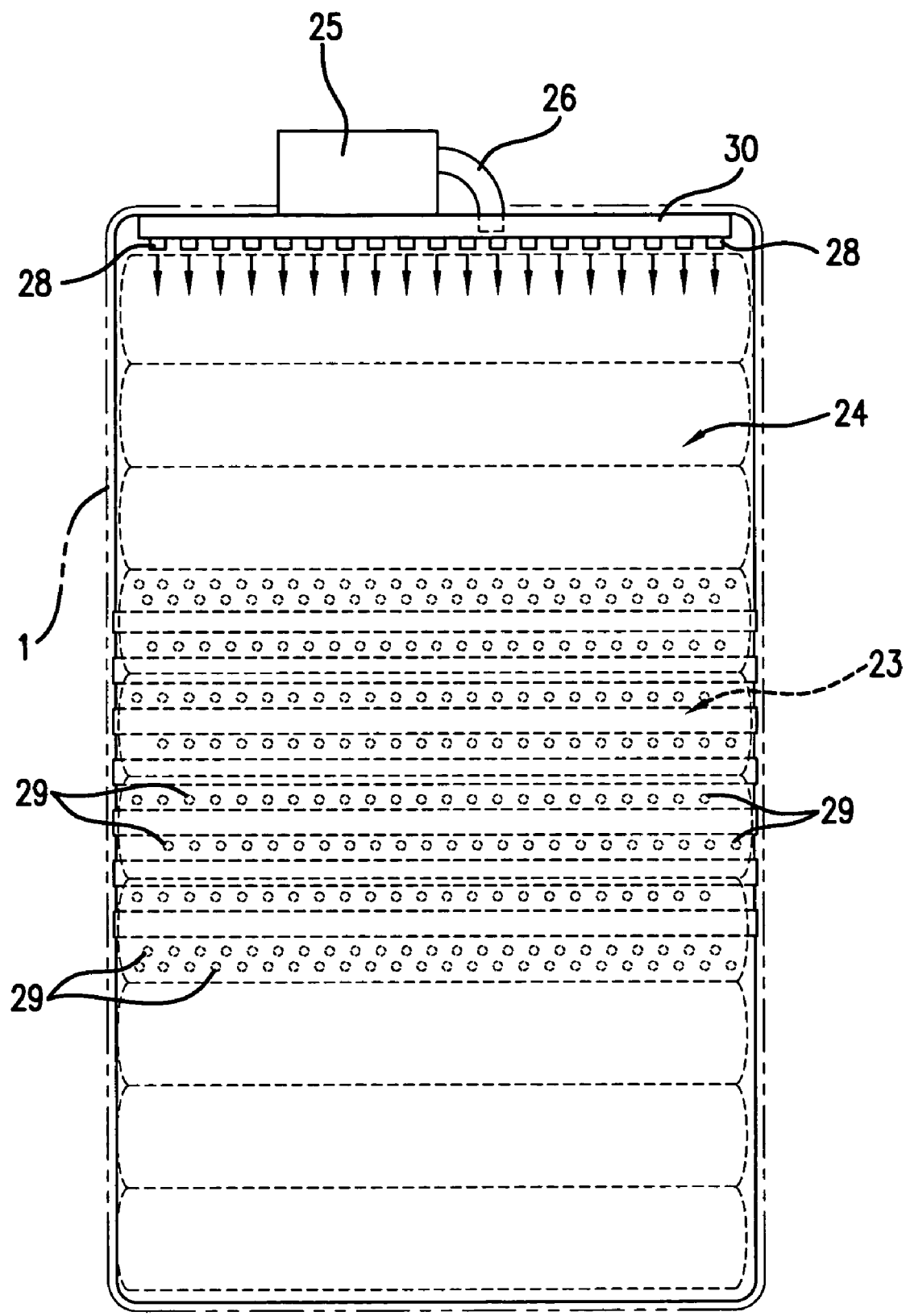
FIG. 13 is a plan view of a mattress according to another embodiment of the invention.
Figure 14:
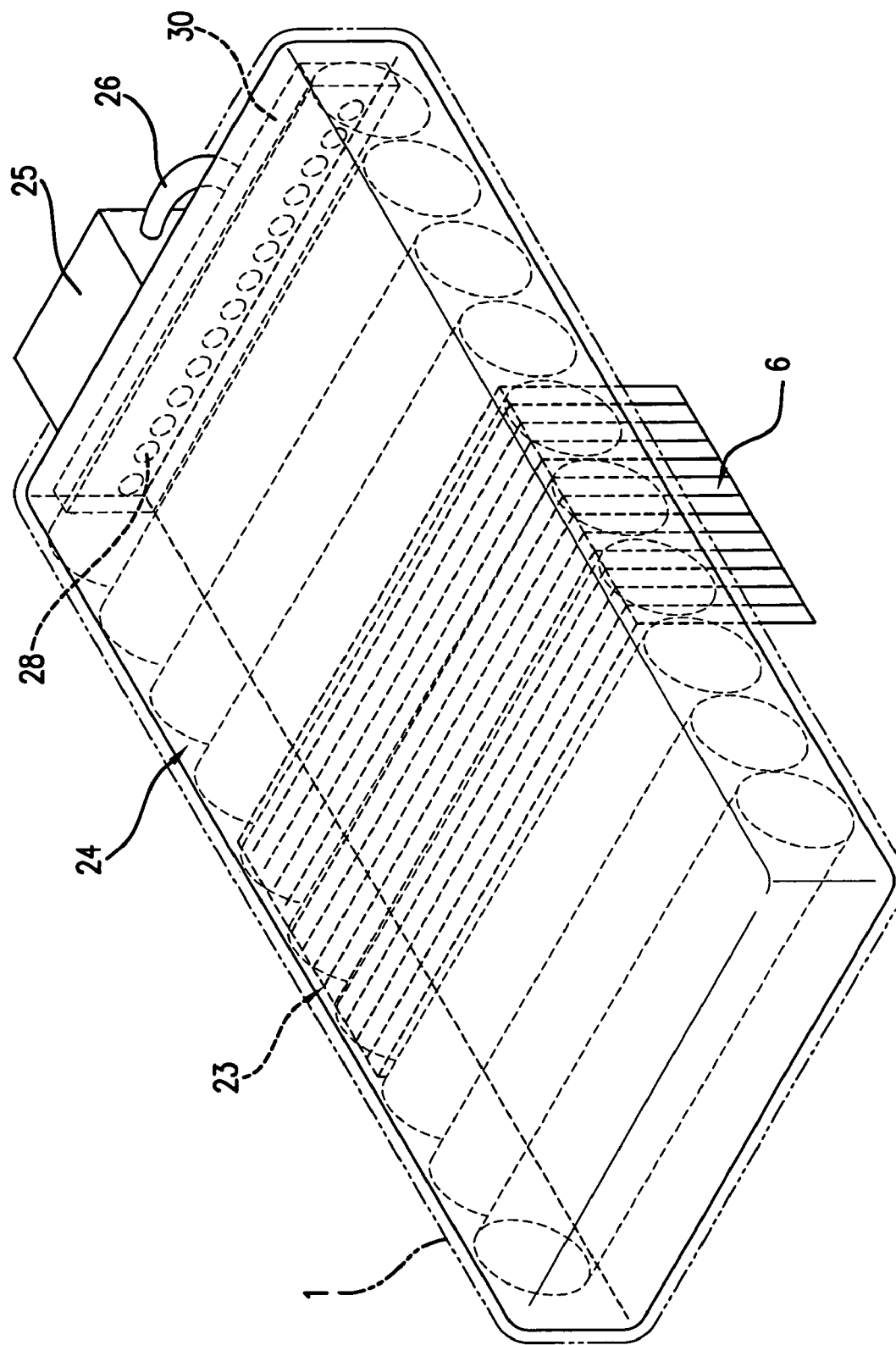
FIG. 14 is a perspective view of a mattress according to an additional embodiment of the invention.

FIGS. 12, 13 and 14 depict the device with surfaces that use power to drive a stream of coolant, which may be air, through the mattress. Such surfaces may be referred to as "low air-loss surfaces". In FIG. 12, the wick 23 is positioned in the region of the powered mattress 24 that supports the region of the body to be cooled, which, as shown, is the central region of the torso and hips. A control box for the mattress that contains the pump or blower unit 25 is present. Air is transported from the box to the mattress through air hose 26, and enters a small manifold 30 along the foot end of the mattress. An air hose oriented transversely to the mattress may be used as a manifold. Air escapes from air vents 28, and streams of air blow through the mattress to carry heat away from the heat wick, particularly in the diffuser region. As a result of this enhanced heat removal from the diffuser region, the temperature gradient between the support region and the diffuser region is increased, thus enhancing cooling.

FIG. 13 is a top view of the wick 23 in use with a slightly different type of low air-loss surface 24. The air stream is vented directly from the support cushions through small holes 29. These vents may be positioned directly under or adjacent to the Heat Wick and once again, function to draw heat away from the wick and into the air stream from which it is expelled from the mattress.

FIG. 14 is a perspective view of a wick 23 in use with a mattress 24 similar in construction to that depicted in FIG. 13 with the air stream directed through the mattress via air vents 29 in a hose or manifold 30. FIG. 14 shows the diffuser regions 6 of the heat wick which, as previously discussed, may be positioned in a number of configurations to exhaust heat. When a heat wick is embedded in or placed on a low air-loss surface as depicted in FIGS. 12, 13, and 14, cooling is most efficient if the diffuser region(s) are positioned to receive at least a portion of the air that is flowing through the mattress. The air stream efficiently withdraws heat from the diffuser regions and as this air is expelled from the mattress into the room, the heat is expelled with it.

Cooling mattresses and mattress inserts, cushions and seat back inserts, overlays, tickings, and bedding materials such as blankets and duvet inserts may be configured to absorb heat from a user's skin and transport this heat to a cooler environment. The non-powered wick can enhance cooling of both non-powered surfaces, such as foam, or powered surfaces that cool the body with moving air, such as low air-loss surfaces. Various materials with high levels of thermal conductivity and mechanical compliance may be configured within a specific range of geometries to cool the skin in a highly effective and cost-effective manner.

The support region may be positioned under the user, for example, as a seat cushion, mattress, or mattress overlay, or against the user, for example, as a seat back, or over the user, for example, as a blanket or a duvet cover.

The heat wick itself is preferred to have no moving parts and no external source of power, relying on geometric configurations of conductive materials to cool the skin. The Conductive Component in the heat wick has high thermal conductivity, is relatively compliant, and therefore comfortable to use. The device should not have excessive levels of electrical conductivity or flammability that may endanger the user.

The Conducting Component has sufficiently high directional thermal conductance to accommodate heat transfer along its length as required by the specific application. The Conducting Component absorbs, transports, and dumps heat. The Conducting Component runs throughout the device, but functions to absorb heat from the skin in the warm support region, and diffuse it to the environment in the cooler diffuser region. The Conducting Component serves a transport function in moving heat from one region to the other. The Conducting Component is essentially a heat conduit or series of conduits that is absorbs heat at one end (the support region), transports it to another end (the diffuser) where it releases heat to the environment. The Conducting Component may be consist of sheets, strips, fibers, or yarns formed of highly conductive materials (typically highly conductive carbon fibers, nanotublules or polymers), or comprised of such materials interleafed or otherwise combined with insulation or cushioning materials. The Conducting Component may be a layer within the heat wick cooling device that comprises layers to enhance durability, cushioning, or otherwise enhance usability.

Preferred embodiments of the invention may be specified as set forth in the numbered paragraphs:

1. The mean conductivity of the Conducting Component between top surface of the conductive layer and the bottom surface of the conductive layer is greater than or equal to 8 W/m-K. This refers to the mean directional conductivity of the entire Conducting Element between conductive surfaces, including the layer(s) of conductive material and any cushioning filler interspersed between these layers, in the direction of preferred heat transfer. The top of this layer is defined as the surface closest to the skin of conductive material (defined as greater than or equal to 8 W/m-K). The bottom of this layer is the surface of the Conducting Component that is farthest from the skin, with this layer being having thermal conductivity greater than or equal to 8 W/m-K. Overall, this entire Conducting Component, which may be comprised of several layers of varying thermal conductivities, has a mean conductivity of greater than or equal to 8 W/m-K in the direction of preferred heat transfer.

2. The surface of Conductive Component closest is preferred to be within 3 inches (7.5 cm) of the body. That is, this Conducting Component may extend to several inches depth but the edge closest to the body is within 3.0 inches of the body when in use. The closest edge of the Conducting Component is within 3.0 inches of the skin whether it is on top of the body (i.e., a blanket) or below it and compressed by the weight of the human body (a cushion or mattress) or pressed against it (a seat back).

3. In the support region, the fibers or bundles of conductive elements are preferred to be oriented to draw heat away from the body and toward a cooler diffuser region. The conductive elements are generally parallel to the surface of the skin in the support region but there may be a relatively small number of bundles in the support region that have a component that is perpendicular to the skin to enhance the flow of heat from the skin to the deeper regions of the conductive layer.

4. Some fiber bundles may be oriented with a component that is perpendicular to the primary direction of heat conduction described above. When present, they are oriented such that a component is perpendicular to the surface. These short, small bundles may be concentrated in the region of maximum cooling requirement, and function to draw heat from the skin/surface interface to deeper levels of the conductive layer(s), to ensure efficient use of the entire conductive layer. Some fibers exhibit very non-uniform conduction characteristics. While they may conduct heat very efficiently along their length, conduction to adjacent parallel fibers is limited, such that deeper fibers should be under utilized without these central perpendicular bundles.

5. The Conducting Element may be enclosed in an envelope of material such as urethane film, or may be enclosed in, or attached to a cloth material, particularly a stretchy cloth such as Lycra. The Conducting Element may or may not be embedded in or adjacent to additional cushioning material such as batting, gel, foam, or elastomer. The conductive elements may be laid between surface layers with no binding or carrier agent, or they may be bound with an adhesive material, to stabilize the fiber positioning and add additional strength with a binding material. Other suitable binding agents include spray urethane, and other glues that maintain conformability when dry.

6. The fibers may be incorporated into the ticking or seat cover, glued or sewed to the underside of the ticking or seat cover, glued or sewed on the mattress underneath the ticking, or interleafed with layer or layers of the ticking as by lamination process.

7. The conductive layer may be incorporated in to the mattress or cushion materials such as foam in a single or multiple layer, interleafing configuration.

8. The Conducting Component is compliant in the support regions so that it deforms significantly under the weight of the body. When the heat wick is positioned in use, a 1.0 kg steel ball placed in the center of the support region of the intact surface (i.e. the surface of a mattress, seat cushion etc. with the cooling device in place) should compress by greater than or equal to 1.0 mm. Alternatively, if the Conducting Component alone is placed on top of a standard foam hospital mattress, a 1.0 kg steel ball placed in the center of the support region should cause the surface of the Conducting Component to compress by greater than or equal to 0.25 mm. There should be sufficient mechanical compliance to the conductive layer so that it is not stiff and uncomfortable to the user.

9. The conductive material required to achieve preferred heat conductivity and transport sufficient heat to cool according to the application of interest may be quantified. The numbers represent the mean directional thermal conductivity k (in Watts per meter degree Kelvin or W/m-K) and the total thickness T in m of the Conducting Component. The two values are specified together because there is an inverse relationship between the mean thermal conductivity k of the material used in the Conductive Component and the thickness of the layer required to conduct sufficient heat to cool the skin under the set of thermal conditions present in the applications of interest here. Table 1 reflects constraints on the conductivity (k) of the material used in the transport layer and the thickness of this layer (T), such that k×T is greater than or equal to 0.006 W/K, and less than or equal to 12 W/K. For typical skin cooling applications of one to five degrees in room temperature settings with the geometries proposed here, k×T in the range of 0.05 to 6 W/K are optimal because a number of applications for this cooling technology have been proposed, a broad range of k×T has been specified to accommodate the various types of geometries that are possible.

k×T greater than or equal to 0.006 and less than or equal to 12 W/K is the overall range of interest specified
  k×T greater than or equal to 0.02 and less than or equal to 10 W/K is the preferred range of interest specified
  k×T greater than or equal to 0.05 and less than or equal to 6 W/K is the highly preferred range of interest specified 10. In some embodiments, the conductive layer is not continuous when viewed from a point not in the plane of the surface. The layer may be separated into parallel strips or bundles of conductive material when viewed from a point perpendicular to the surface such as above a mattress or in front of a seat back. For example, in one embodiment for use with an air cell mattress or cushion, the conductive material is positioned between the air cells that may form a grid or run perpendicular to the body. In such cases, the k×T requirement applies to the mean thickness of conductive material across the region to be cooled, including these separations between bundles. Sections of conductive material separated by a distance greater than 0.20 m (20 cm) when viewed from a point perpendicular to the surface, however, are to be treated as separate cooling regions with respect to the k×T criterion.

The conductive layers may be positioned only in the central region of the bed or seat to cool the buttocks and/or low back, and may be positioned at any location on the bed, seat, or seat back surface to cool different regions of the body or, in some cases, may be positioned to cool the entire body. For non-mattress applications such as wheel chair, office, residential, or vehicle seating, the specifications are essentially the same as for mattresses: the conductive elements may be distributed across the entire seat cushion and seat back. Conductive materials can now be purchased in a variety of thermal conductivity levels and the selection of the appropriate material is based on cost, mechanical characteristics, electrical characteristics (high electrical conductivity is undesirable for a support material in the hospital environment), etc. The table below gives additional specificity as to the quantity of thermally conductive material required.

The Table contains only the first range listed in #9 above. This is the Overall Range of interest. We have also specified a Preferred Range (B.) and a Highly Preferred Range (C.)

TABLE 1

Depth of Conductive Material required for Given Conductivity
Overall Range Specification: k × T greater than or equal to 0.006 and less than or equal to 12 W/K

| Conductivity (W/m–K) | Minimum Depth Required | | Maximum Depth Required | |
|---|---|---|---|---|
| | (m) | (cm) | (m) | (cm) |
| 10 | 0.000600 | 0.060 | 1.200 | 120.00 |
| 40 | 0.000150 | 0.015 | 0.300 | 30.00 |
| 60 | 0.000100 | 0.010 | 0.200 | 20.00 |
| 80 | 0.000075 | 0.008 | 0.150 | 15.00 |
| 100 | 0.000060 | 0.006 | 0.120 | 12.00 |
| 125 | 0.000048 | 0.005 | 0.096 | 9.60 |
| 150 | 0.000040 | 0.004 | 0.080 | 8.00 |
| 200 | 0.000030 | 0.0030 | 0.060 | 6.00 |
| 300 | 0.000020 | 0.0020 | 0.040 | 4.00 |
| 500 | 0.000012 | 0.0012 | 0.024 | 2.40 |
| 1000 | 0.000006 | 0.0006 | 0.012 | 1.20 |
| 2000 | 0.000003 | 0.0003 | 0.006 | 0.60 |

The fiber orientation is preferred because conductivity is typically oriented disproportionately along the axis of the fibers or wire. The filaments normally lie parallel to the surface of the mattress or seat and conduct heat away from the body. To ensure that significant lateral conduction, i.e., parallel to the skin/support surface interface, occurs in the deeper levels of the conductive fiber layer or layers, a small number of highly conductive fiber bundles oriented perpendicular to the surface in the primary region of cooling in the center of the mattress or seat may be used.

All configurations of conductive layers, fibers, or fiber bundles may be used inside the ticking, or outside the ticking, as a mattress or seating overlay. A preferred use is as a secondary overlay in which the cooling device is placed on top of a mattress, cushion, or seat back to enhance cooling but underneath a second overlay that has been selected for its comfort or cushioning characteristics.

In the non-powered embodiments, tThe thermal diffuser regions are equivalent in function to that of a radiator in a typical heat transfer application. However, in many of the applications described in which the thermal diffuser is underneath a ticking and bedding, the bulk of the heat sinking from the diffuser is done not by radiation but conduction to the surface of the mattress ticking and bedding materials. Heat is released from this outer surface to the environment primarily by radiation and convection. For this reason, the term "thermal diffuser" is used, because it transports heat from the support surface to the environment by any of the possible modes of heat transfer, and not only by radiation. In the embodiments shown in FIGS. 16 through 19, heat is also withdrawn from the diffuser region by means of a small, powered cooling unit such as a thermoelectric module.

The thermal diffuser regions may be positioned at the distal regions of the support surface or blanket, away from the region to be cooled, such that heat conducted from the warm central region flows to this cooler diffuser area. The diffuser(s) may be along the top surface of the bed or seat, along the periphery, and/or it may extend to the sides of the surface, such as the edges of the bed or seat. Another preferred position is for the diffuser regions to simply hang down below the bed or seat for exposure to the cool air under the bed or chair. They may also extend to the opposite side of the support surface, such that they extend underneath the bed, underneath a seat, or around to the back side of a seat back.

The thermal diffuser regions may be thermally connected to the thermal conduction layer of the support surface. That is, they may substantially overlap the conductive layer in the support region or, if there is 1.0 cm or more of material between the conductive layer of the support region and the thermal diffuser region, this intermediate material has thermal conductivity k>8 W/m-K to ensure adequate flow of heat from warm support regions to the diffuser regions. Typically, the thermal diffuser material may be very similar to, if not identical to that of the conductive layer in the support region. The diffuser is the region of the conductive layer that extends substantially away from the support region to increase the heat exhaustion area.

The thermal diffuser is constructed of material with high thermal conductivity (greater than or equal to 8 W/m-K). Some suitable materials for this purpose are pitch-based carbon fiber fibers (50-1100 W/m-K and developing rapidly) or conductive polymers. Metals may be acceptable in some applications.

The thermal diffuser may comprise conductive cloth, strips, sheets, foils, louvers or fibers, yarn, or fabric woven of conductive material. The diffuser may, in some applications, be enclosed in or attached to a protective covering. The thickness of the Conductive Element in the diffuser area conforms to a k×T criterion (see Table 1) of k×T>0.001 W/K and ≦10 W/K. Somewhat more flexibility in the k×T of the diffuser is required to accommodate different area requirements based on surface geometries.

The surface area of the thermal diffuser may be variable, depending on the application because the amount of heat to be exhausted, and the heat transfer conditions from the diffuser surface. In general, however, the surface area is at least 0.25 times as great as the area of the body that is being cooled. Under typical heat transfer conditions, the diffuser area is 1.5 to 5.0 times the area of the region of the body to be cooled. In less favorable environments or when more cooling is required, the area may be 10 or more times the area of the body to be cooled.

Figure 15:
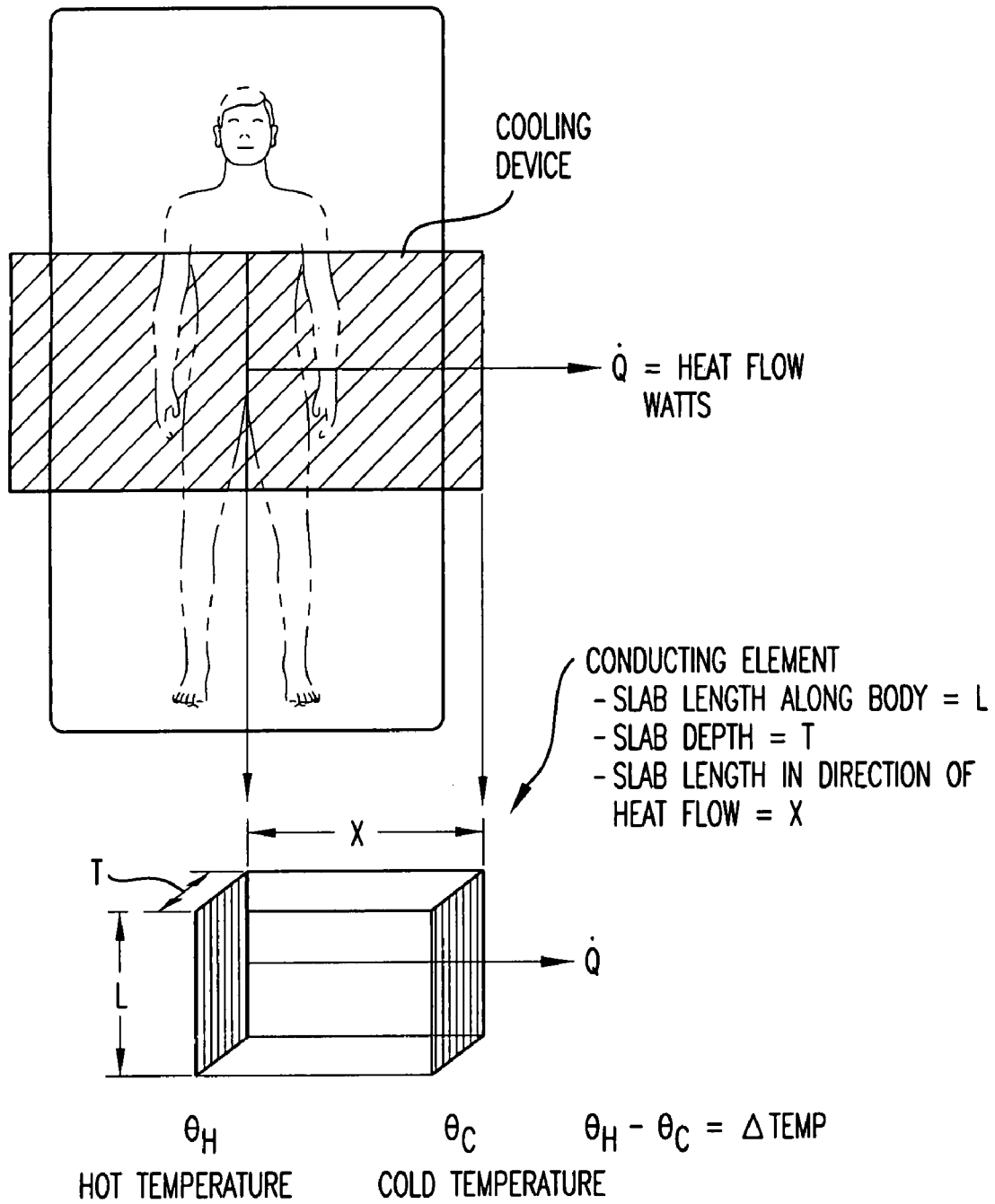
FIG. 15 demonstrates heat transfer in an idealized support surface.

The capabilities are specified to an extent by the k×T parameter presented in 9 above and in Table 2. FIG. 15 represents a uniform slab of material with mean thermal conductivity k in the direction of heat flow shown. This is an idealized version of the Conducing Element. The left face is maintained at temperature $\theta_{Hot}$ by the body and the right face is maintained at $\theta_{Cold}$ by its exposure to ambient air. All other faces of the slab are insulated so that no heat flows across them. Under these conditions, heat flows through the slab from the hot face to the cold face at a rate described by Fourier's Law:

$$\frac{dQ}{dt} = \frac{k*A}{X} * (\theta_{Hot} - \theta_{Cold}) \quad (1)$$

Where:

Q=quantity of heat in Joules (J)

$\frac{dQ}{dt}$ = flow of heat in Joules/sec or Watts (W)

k=mean thermal conductivity in Watts/m-K (Watts per meter degree Kelvin). Also note here that small case k denotes conductivity while capital K refers to temperature Kelvin A=Area of slab perpendicular to the direction of heat flow in square meters (m²)

L=length of slab in direction of long axis of body. In other words, this is the length of the body to be cooled (m)

T=thickness of lab (m)

X=Length of conduction path in meters. In the figure below, this is the distance from the hot face to the cold face of the slab in meters (m).

$\theta_{Hot} - \theta_{Cold}$=Temperature difference between hot and cold faces of slab in degrees K (K).

The cross-sectional area of the slab is T×L. Rearranging (1) gives:

$$\frac{\frac{dQ}{dt}}{L} = k*T*\left(\frac{\Delta\theta}{X}\right) \quad (2)$$

Using equation (2), it is clear that the specified quantity k×T can be used to calculate the amount of heat per unit length of the body that can be withdrawn under a set of environmental constraints. Δθ and X are constraints that are set by the application: Δθ is the temperature difference between the support and the diffuser regions and X is the distance between them. The k×T parameter therefore is an attempt to quantify a range of constraints on the thickness and conductivity of the Conducting Element to ensure that the device can perform the skin cooling function in the expected range of environments (i.e., thermal and geometric) in which it performs.

Figure 16:
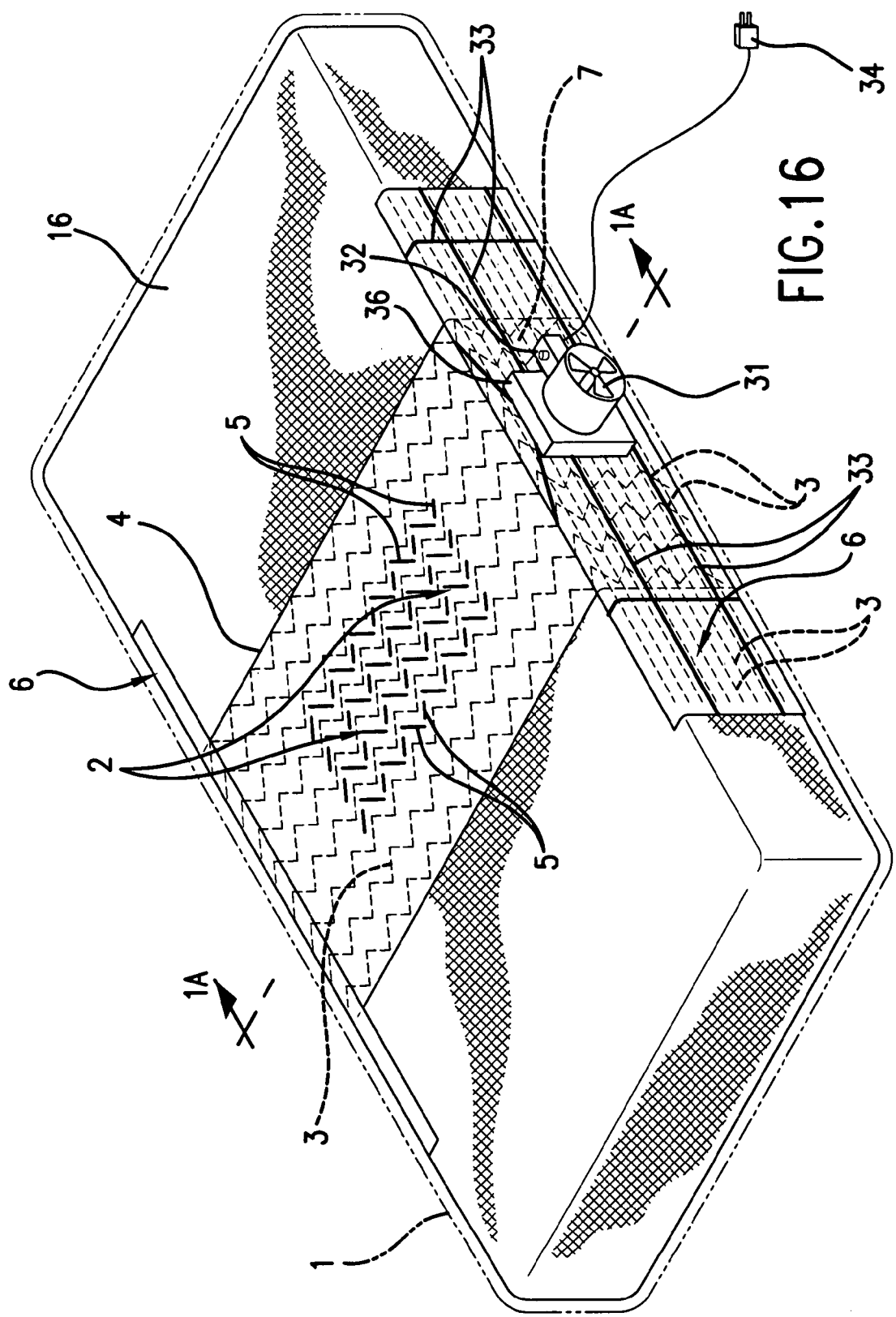
FIG. 16 is a perspective view of another embodiment of the mattress with a powered cooling module attached to the heat sink region.

FIGS. 16 through 19 present powered embodiments in which heat is withdrawn from the diffuser region by means of a thermo-electric or similar compact chilling unit. In FIG. 16, the powered heat wick is shown in use under the ticking of a standard mattress. Heat from the diffuser 6 is rapidly withdrawn by means of a cooling unit 36. Heat is directionally channeled from throughout the diffuser region to this cooling unit by means of Thermal Guide Strips 33. These highly conductive strips (minimum 40 W/m-K and having fibers with thermal conductivity>120 W/m-K) ensure that the heat that reaches the periphery of the surface is directed toward the thermo electric module. A control unit 32 is included to adjust cooling power. A small fan 31 is attached to the cooling unit to dissipate heat.

Figure 17:
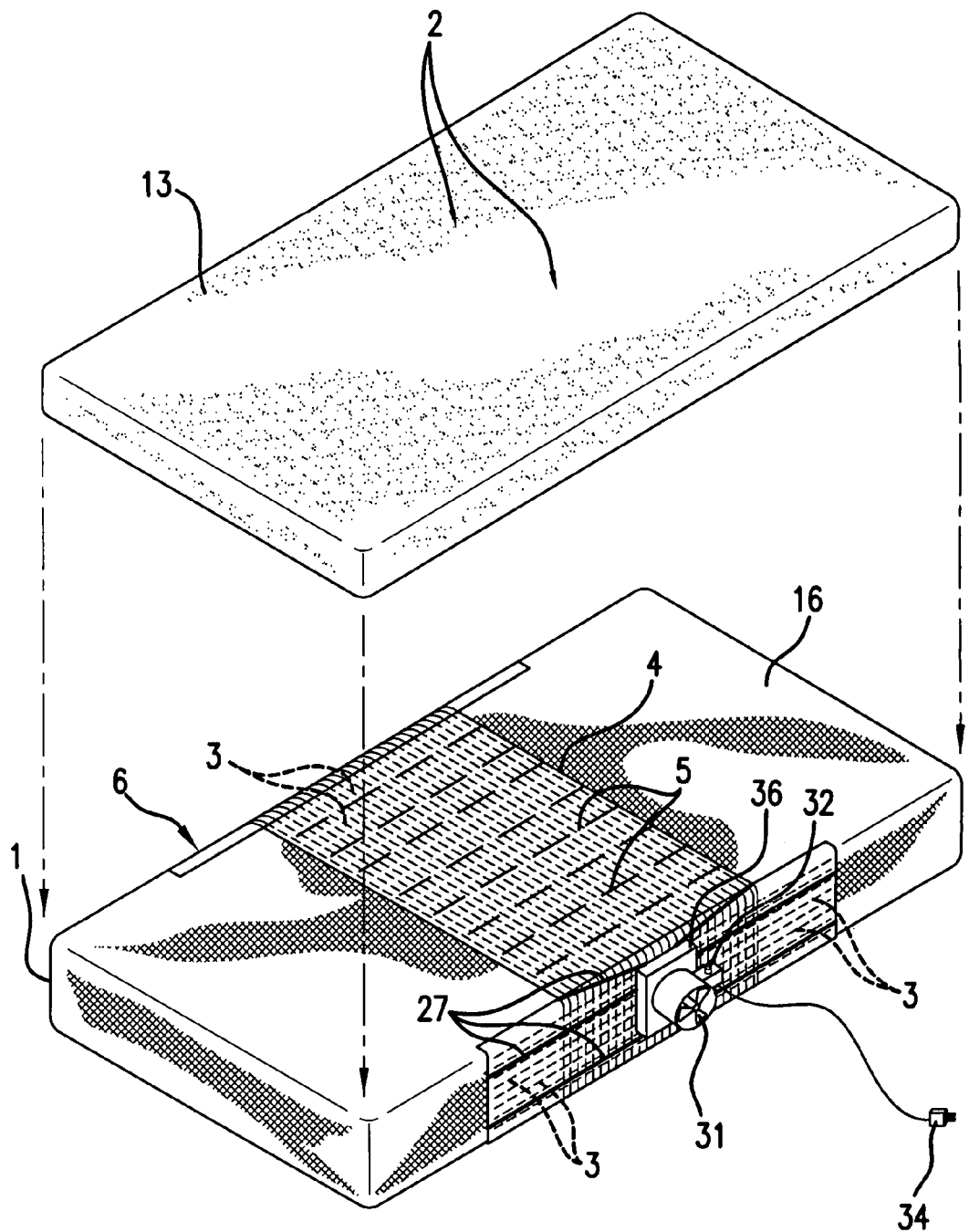
FIG. 17 is a perspective view of one embodiment of the heat with a powered cooling module attached to the heat sink region. The heat wick is in use on top of a mattress and beneath a mattress overlay.

Another powered heat wick is shown in FIG. 17. The heat wick is in use between a standard mattress 16 and a mattress overlay 13.

Figure 18:
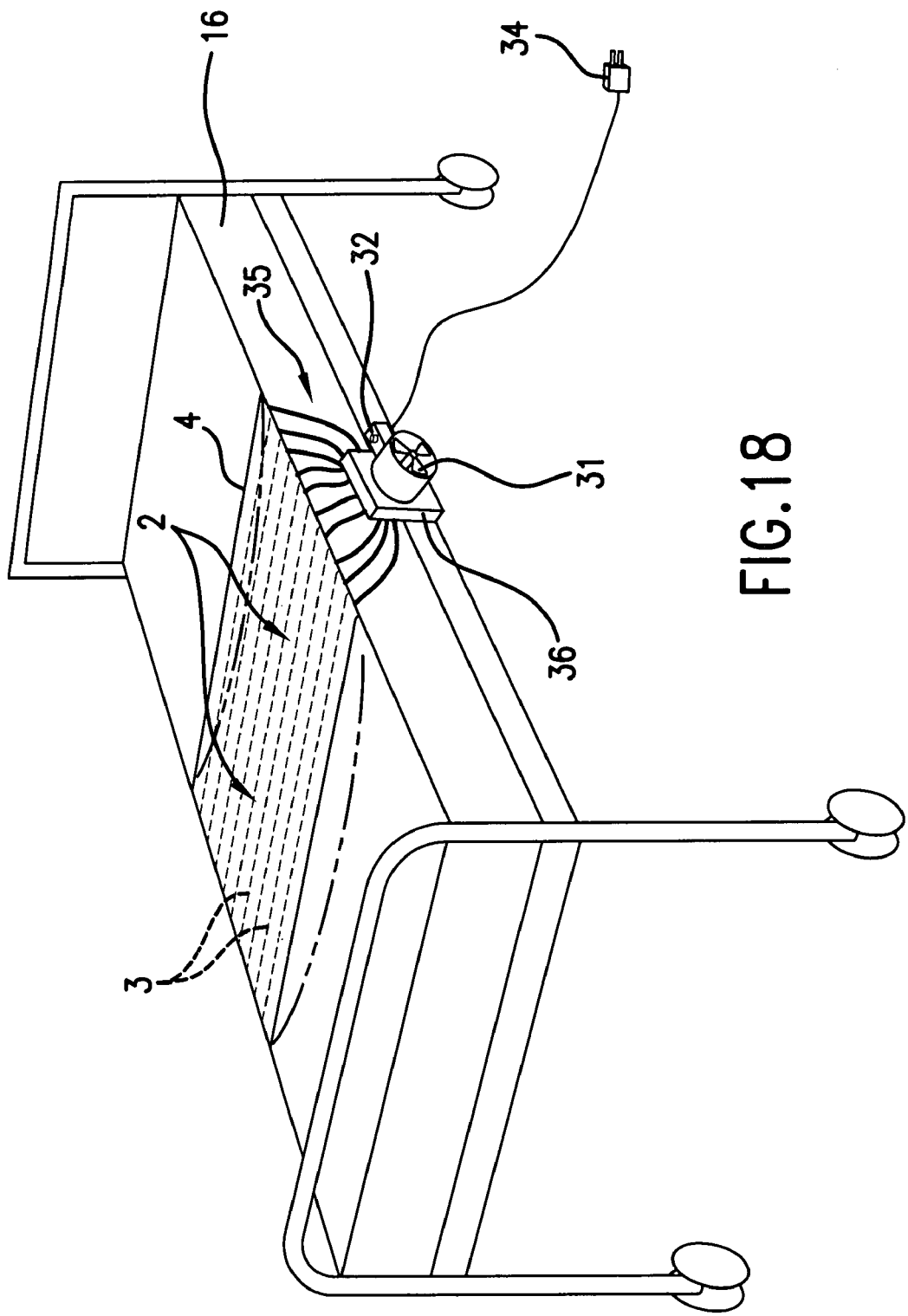
FIG. 18 is a perspective view of another embodiment of the mattress with a powered cooling module attached to a funnel-shaped heat sink region.

In FIG. 18, another embodiment is depicted in which the heat is channeled to the cooling unit 36 via a "heat funneling region" 35. The diffuser fibers are drawn to converge at the cooling unit.

Figure 19:
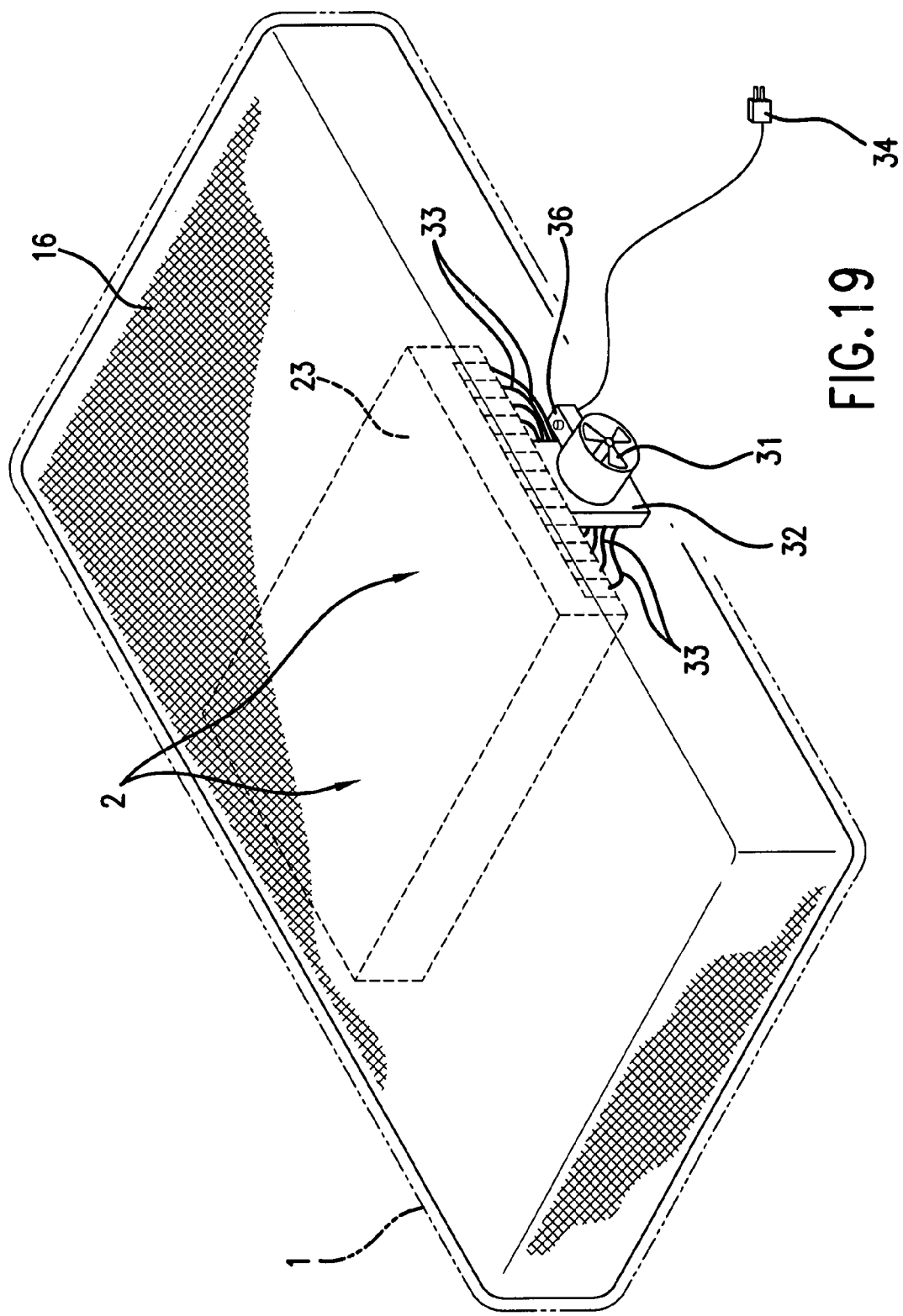
FIG. 19 is a perspective view of another embodiment of the mattress with a powered cooling module attached to the heat sink region that is positioned beneath the mattress.

FIG. 19 depicts an embodiment in which the cooling unit 36, fan 31, and control module 32 are configured beneath the mattress. In this embodiment, the heat is directed to the cooling region via the thermal guide strips 33 as shown, or by a heat funneling region as shown in the previous figure.

From the foregoing it can be realized that the described devices of the present inventions may be utilized as a therapeutic support surface, such as a mattress, mattress overlay, a wheel chair cushion, seat cushion or seat back or seat overlay for home, office, or vehicle applications.

Brief List of Numbers Used in Drawings 1. ticking or covering of mattress
2. support region: region of the support surface (mattress, mattress overlay, seat cushion or seat back) intended to be close to, adjacent to or in contact with the body
3. conductive material (typically high thermal
4. conductivity carbon fibers, polymers or nanotubules)
5. thin envelope or layer of protective sheeting (such as urethane) or fabric (such as Lycra) that encases conductive material)
6. slits, which may or may not be added o the envelope or protective sheet material to enhance the distension of the surface to accommodate weight loading.
7. thermal diffuser region: the cooler region at the edge of the support surface to which the body's heat is transported. From the thermal diffuser, it is transported to the cooler environment by air flowing past it or conduction to adjacent materials
8. Overlap of material from support region and diffuser region to ensure continuity of heat conduction path
9. Individual cells of support surface
10. thermally conductive strips between cells to cool these cells
11. multi strip thermal diffuser region of embodiment appropriate for multi-cell mattress or seat: strips simply extend to the cooler edge of surface and dissipate heat directly to environment.
12. sheet-shaped thermal diffuser region of embodiment appropriate for multi-cell mattress or seat. (Thermally conductive strips join or overlap broader area sheet to enhance heat dissipation)
13. Base cushion beneath air cells with conductive material built into it. The base cushion extends to periphery where it forms diffuser region. #12 therefore indicates the conductive material that is both underneath the support region and extending to the periphery to form the diffuser region.
14. Mattress overlay that may or may not be used with conductive device, which is placed on top of mattress and ticking in this configuration
15. base cushion at bottom of seat cushion or rear of seat back to prevent bottoming out
16. Periphery of seat which may include conductive material at edge to form thermal diffuse
17. standard mattress that conductive cooling device can be placed on top of, placed inside of, or built into.
18. cooling insert that can be placed in duvet (blanket cover) of a cooling blanket
19. blanket cover or duvet that cooling blanket can be slipped inside to enhance comfort and provide protection
20. structural sheet or blanket to which cooling elements can be attached
21. support region of cooling blanket
22. diffuser region of cooling blanket
23. thermally conductive strips that may or may not be covered for protection
24. embedded conducting cooling wick
25. Powered air surface to which non-powered wick has been added to enhance cooling
26. Control box for air surface with blower
27. Air hose that takes air from control/blower box to powered air surface to which non-powered wick has been added or built into
28. Air bladders of air surface
29. Air vents from which air is blown into the mattress and ultimately across the non-powered wick to enhance cooling.
30. Vents in cushions of low-air loss air surface that blow air onto the non-powered wick to enhance cooling.
31. Manifold from which air vents into mattress thermo electric module for cooling or warming the "heat sink" region.
32. heat sink/fan assembly to enhance steady state dissipation of heat from the thermo electric module
33. control unit for thermo electric module and heat sink assembly. This allows us to control power input and thus to adjust the level of cooling or warming
34. Thermal Guide Strips. These are very high conductivity strips (minimum 40 W/m-K but typically composed of fibers with thermal conductivity>120 W/m-K) that ensure that the heat that reaches the periphery of the surface is directed toward the thermo electric module.
35. Power cord. This unit requires power but it can be supplied by battery, generator, or wall input.
36. Heat funneling region: the conductive materials in the heat sink region are drawn together of "funneled" to the Thermo electric module.
37. Thermo-electric module or similar compact cooling unit

What is claimed is:

1. A thermally conductive support surface, comprising:
   (a) a cushion having a generally planar surface, said generally planar surface comprising a first set of thermally conductive fibers; and
   (b) a thermal diffuser comprised of a second set of thermally conductive fibers that thermally communicates with said first set of thermally conductive fibers, wherein said thermal diffuser extends beyond said generally planar surface, wherein said thermal conductivity of said cushion is greater than eight (8) watts per meter-degree Kelvin.

2. The thermally conductive support surface as described in claim 1, wherein said cushion is centrally disposed within said thermally conductive support surface, and said diffuser is present on a periphery of said thermally conductive support surface.

3. The thermally conductive support surface as described in claim 1, wherein said thermally conductive fibers of said cushion comprises carbon fiber.

4. The thermally conductive support surface as described in claim 1, wherein said diffuser comprises carbon fiber.

5. The thermally conductive support surface as described in claim 3, wherein said diffuser comprises carbon fiber.

6. The thermally conductive support surface as described in claim 1, wherein a fluid is forced past said diffuser, and said fluid removes heat from said diffuser.

7. The thermally conductive support surface as described in claim 1, wherein said diffuser extends beyond an edge of said cushion.

8. The thermally conductive support surface as described in claim 1, wherein said diffuser has a surface that is opposite said generally planar surface, and wherein said diffuser extends beyond an edge of said surface that is opposite said generally planar surface.

9. A thermally conductive support surface, comprising:
   (a) a cushion having a generally planar surface, said generally planar surface comprising a first set thermally conductive fibers;
   (b) a thermal diffuser comprised of a second set of thermally conductive fibers that thermally communicates with said first set of thermally conductive fibers, wherein said thermal diffuser extends beyond said generally planar surface, wherein said thermal conductivity of said cushion is greater than eight (8) watts per meter-degree Kelvin; and (c) a powered cooling device that thermally communicates with said thermal diffuser.

10. The thermally conductive support surface as described in claim 9, wherein said cushion is centrally disposed within said thermally conductive support surface, and said diffuser is present on a periphery of said thermally conductive support surface.

11. The thermally conductive support surface as described in claim 9, wherein said thermally conductive fibers of said cushion comprises carbon fiber.

12. The thermally conductive support surface as described in claim 9, wherein said diffuser comprises carbon fiber.

13. The thermally conductive support surface as described in claim 11, wherein said diffuser comprises carbon fiber.

14. The thermally conductive support surface as described in claim 9, wherein a fluid is forced past said diffuser, and said fluid removes heat from said diffuser.

15. The thermally conductive support surface as described in claim 9, wherein said diffuser extends beyond an edge of said cushion.

16. The thermally conductive support surface as described in claim 9, wherein said has a surface that is opposite said generally planar surface, and wherein said diffuser extends beyond an edge of said surface that is opposite said generally planar surface.

17. The thermally conductive support surface as described in claim 9, wherein said powered cooling device is thermoelectric.

* * * * *